(12) United States Patent
Brooks et al.

(10) Patent No.: US 10,392,474 B2
(45) Date of Patent: Aug. 27, 2019

(54) ANIONIC LINEAR POLYGLYCEROL DERIVATIVES, A METHOD FOR MANUFACTURING AND APPLICATIONS

(71) Applicants: FREIE UNIVERSITAET BERLIN, Berlin (DE); THE UNIVERSITY OF BRITISH COLUMBIA, Vancouver (CA)

(72) Inventors: Donald Brooks, Vancouver (CA); Jayachandran Kizhakkedathu, New Westminster (CA); Rajesh Shenoi, Alappuzha (IN); Marie Weinhart, Berlin (DE); Benjamin Lai, Vancouver (CA); Rainer Haag, Berlin (DE); Dominic Groeger, Berlin (DE)

(73) Assignees: FREIE UNIVERSITAET BERLIN, Berlin (DE); THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 15/545,272

(22) PCT Filed: Jan. 20, 2016

(86) PCT No.: PCT/EP2016/051097
§ 371 (c)(1),
(2) Date: Jul. 20, 2017

(87) PCT Pub. No.: WO2016/116489
PCT Pub. Date: Jul. 28, 2016

(65) Prior Publication Data
US 2018/0009943 A1    Jan. 11, 2018

(30) Foreign Application Priority Data
Jan. 20, 2015 (EP) .................................. 15151794

(51) Int. Cl.
C08G 65/32      (2006.01)
C08G 65/334     (2006.01)
A61K 31/255     (2006.01)
A61K 38/36      (2006.01)

(52) U.S. Cl.
CPC ........ *C08G 65/3344* (2013.01); *A61K 31/255* (2013.01); *A61K 38/36* (2013.01); *C08G 65/32* (2013.01); *C08G 2650/54* (2013.01)

(58) Field of Classification Search
CPC ............... C08G 65/3344; C08G 65/32; C08G 2650/54; A61K 38/36; A61K 31/255
See application file for complete search history.

(56) References Cited

U.S. PATENT DOCUMENTS 8,637,008 B2   1/2014   Kizhakkedathu et al.

FOREIGN PATENT DOCUMENTS

| DE | 10 2006 027 125 A1 | 12/2007 | | |
|---|---|---|---|---|
| WO | 2008/015015 A2 | 2/2008 | | |
| WO | WO 2008015015 A2 | * | 2/2008 | |
| WO | WO-2008015015 A2 | * | 2/2008 | ........... C08G 83/003 |
| WO | 2011/095311 A1 | 8/2011 | | |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Gervais et al, Macromolecules, Direct Synthesis of a-Azido,w-hydroxypolyethers by Monomer-Activated Anionic Polymerization, 2009, 42, pp. 2395-2400. (Year: 2009).*
Kohler et al, Chemical Communications, Post-polymerization functionalization of linear polyglycidol with diethyl vinylphosphonate, 2011,47, pp. 8148-8450 and S1-S11 . (Year: 2011).*
Kainthan et al, Biomacromolecules, Biocompatibility Testing of Branched and Linear Polyglycidol, 2006, 7, pp. 703-709. (Year: 2006).*
Bock et al., "Activation of intrinsic blood coagulation by Ellagic Acid: Insoluble Ellagic Acid-Metal Ion Complexes Are the Activating Species", Biochemistry, vol. 20, Issue 25, Dec. 1981, pp. 7258-7266.
Calderón et al., "Dendritic polyglycerols for biomedical applications", Advanced Materials, vol. 22, Issue 2, Jan. 12, 2010, pp. 190-218.
Caterina et al., "Anticoagulants in heart disease: current status and perspectives", European Heart Journal, vol. 28, Issue 7, 2007, pp. 880-913.
Coombe and Kett, "Heparin—A Century of Progress", Handbook of Experimental Pharmacology, Springer Berlin Heidelberg, vol. 207, 2012, pp. 361-383.
Davie and Ratnoff, "Waterfall Sequence for Intrinsic Blood Clotting", Science, vol. 145, Issue 3638, Sep. 18, 1964, pp. 1310-1312.
Davie, "A Brief Historical Review of the Waterfall/Cascade of Blood Coagulation", Journal of Biological Chemistry, vol. 278, Issue 51, 2003, pp. 50819-50832.
Dernedde et al., "Dendritic polyglycerol sulfates as multivalent inhibitors of inflammation", Proceedings of the National Academy of Sciences of the United States of America, vol. 107, Issue 46, 2010, pp. 19679-19684.
Fauci et al, "Harrison's Principles of Internal Medicine", Mc Graw Hill Medical, 17th Edition ed., 2008, pp. 1-491.
Georgievski et al., "Non-Fouling Poly(ethylene oxide) Layers End-Tethered to Polydopamine", Langmuir, vol. 28, Issue 40, 2012, pp. 14273-14283.
Gervais et al., "Direct Synthesis of α-Azido,ω-hydroxypolyethers by Monomer-Activated Anionic Polymerization", Macromolecules, vol. 42, Issue 7, 2009, pp. 2395-2400.

(Continued)

Primary Examiner — Paul A Zucker
(74) Attorney, Agent, or Firm — Maschoff Brennan

(57) ABSTRACT

The invention relates to a linear polyglycerol compound, comprising a backbone of linearly linked glycerol residues. This compound is characterized in that it carries a plurality of substituents in the nature of covalently bound sulfates, wherein a degree of substitution of the backbone is preferably between 30 and 100%. A method of manufacturing the compound as well as uses of this compound and similar compounds are also disclosed.

16 Claims, 14 Drawing Sheets

(56) References Cited

OTHER PUBLICATIONS

Gervais et al., "Synthesis of Linear High Molar Mass Glycidol-Based Polymers by Monomer-Activated Anionic Polymerization", Macromolecules, vol. 43, Issue 4, 2010, pp. 1778-1784.
Gray et al., "Heparin and low-molecular-weight heparin", Thrombosis and Haemostasis, vol. 99, 2008, pp. 807-818.
Hawkins and Evans, "Minimising the risk of heparin-induced osteoporosis during pregnancy", Expert Opinion on Drug Safety, vol. 4, Issue 3, May 10, 2005, pp. 583-590.
Hirsh and Raschke, "Heparin and low-molecular-weight heparin: the Seventh ACCP Conference on Antithrombotic and Thrombolytic Therapy", Chest, vol. 126, Issue 3 Supplement, Sep. 2004, pp. 188S-203S.
Hirsh et al., "Guide to Anticoagulant Therapy: Heparin A Statement for Healthcare Professionals From the American Heart Association", Circulation, vol. 103, Issue 24, Jun. 19, 2001, pp. 2994-3018.
Jang and Hursting, "When Heparins Promote Thrombosis Review of Heparin-Induced Thrombocytopenia", Circulation, vol. 111, Issue 20, May 24, 2005, pp. 2671-2683.
Kainthan and Brooks, "In vivo biological evaluation of high molecular weight hyperbranched polyglycerols", Biomaterials, vol. 28, Issue 32, Nov. 2007, pp. 4779-4787.
Kainthan et al., "Biocompatibility testing of branched and linear polyglycidol", Biomacromolecules, vol. 7, Issue 3, Feb. 2006, pp. 703-709.
Kainthan et al., "In vitro biological evaluation of high molecular weight hyperbranched polyglycerols", Biomaterials, vol. 28, Issue 31, Nov. 2007, pp. 4581-4590.
Köhler et al., "Electronic supporting information Post-polymerization functionalization of linear polyglycidol with diethyl vinylphosphonate", accessed at http://www.rsc.org/suppdata/cc/c1/c1cc12484f/c1cc12484f.pdf, accessed on Jul. 5, 2017, pp. 11.
Köhler et al., "Post-polymerization functionalization of linear polyglycidol with diethyl vinylphosphonate", Chemical Communications, vol. 47, Issue 28, Jun. 10, 2011, pp. 8148-8150.
Li and Chau, "Synthesis of Linear Polyether Polyol Derivatives As New Materials for Bioconjugation", Bioconjugate Chemistry, vol. 20, Issue 4, Apr. 15, 2009, pp. 780-789.
Liu et al., "Improved coagulation in bleeding disorders by Non-Anticoagulant Sulfated Polysaccharides (NASP)", Thrombosis and Haemostasis, vol. 95, Issue 1, 2006, pp. 68-76.
Nimjee et al., "The potential of aptamers as anticoagulants", Trends in Cardiovascular Medicine, vol. 15, Issue 1, Jan. 2005, pp. 41-45.
Nisio et al., "Direct Thrombin Inhibitors", New England Journal of Medicine, vol. 353, Issue 10, Sep. 8, 2005, pp. 1028-1040.
Pai and Crowther, "Neutralization of Heparin Activity", Handbook of Experimental Pharmacology, vol. 207, 2012, pp. 265-277.
Shenoi et al., "Affinity-based design of a synthetic universal reversal agent for heparin anticoagulants", Science Translational Medicine, vol. 6, Issue 260, Oct. 29, 2014, pp. 14.
Tanaka et al., "Blood coagulation: hemostasis and thrombin regulation", Anesthesia & Analgesia, vol. 108, Issue 5, 2009, pp. 1433-1446.
Thomas et al., "Beyond Poly(ethylene glycol): Linear Polyglycerol as a Multifunctional Polyether for Biomedical and Pharmaceutical Applications", Biomacromolecules, vol. 15, Issue 6, 2014, pp. 1935-1954.
Türk et al., "Dendritic polyglycerol sulfates as new heparin analogues and potent inhibitors of the complement system", Bioconjugate Chemistry, vol. 15, Issue 1, 2004, pp. 162-167.
Visentin et al., "Heparin is not required for detection of antibodies associated with heparin-induced thrombocytopenia/thrombosis", Journal of Laboratory and Clinical Medicine, vol. 138, Issue 1, Jul. 2001, pp. 22-31.
Weinhart et al., "Linear poly(methyl glycerol) and linear polyglycerol as potent protein and cell resistant alternatives to poly(ethylene glycol)", Chemistry—An Asian Journal, vol. 5, Issue 9, Sep. 3, 2010, pp. 1992-2000.
Wilson, J., "Heparin Sodium—A Review (The Continuing Battle for Standardization)". Journal of Extra-Corporeal Technology., vol. 6, Issue 4, 1974, pp. 207-213.
Extended European Search Report dated Jun. 25, 2015 as received in Application No. 15151794.3.

* cited by examiner

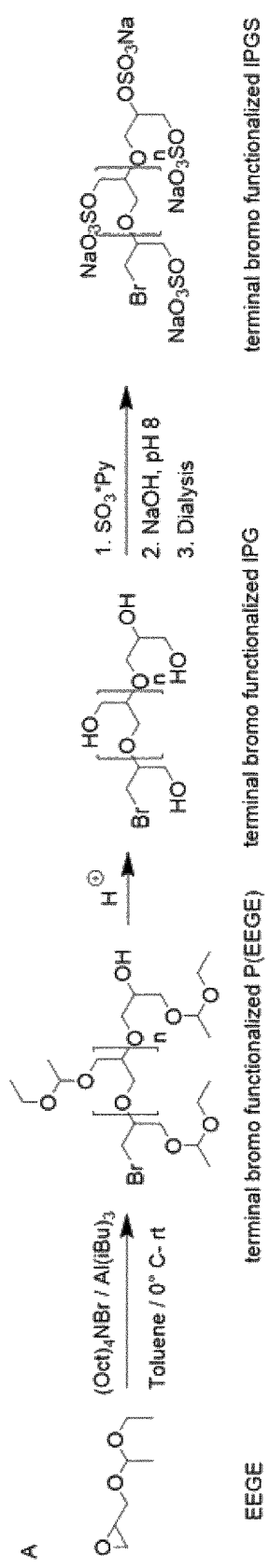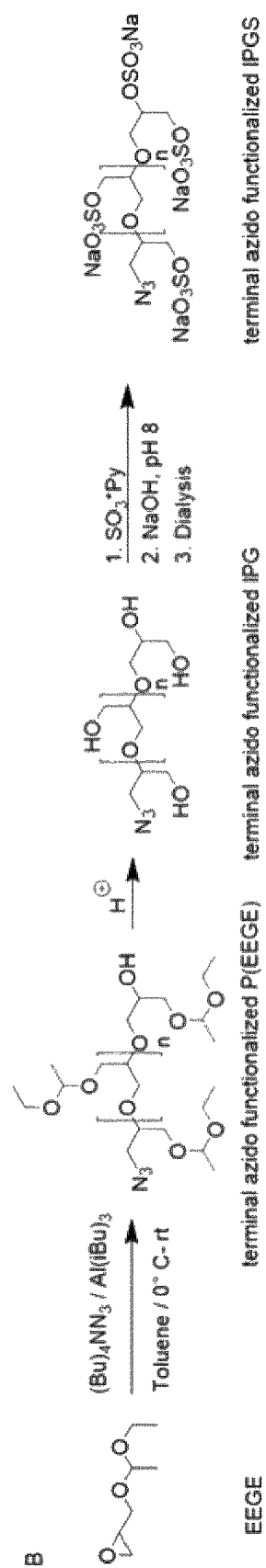
FIG 3A
FIG 3B

ANIONIC LINEAR POLYGLYCEROL DERIVATIVES, A METHOD FOR MANUFACTURING AND APPLICATIONS

CROSS-REFERENCE TO A RELATED APPLICATION

This application is a National Phase Patent Application of International Patent Application Number PCT/EP2016/051097, filed on Jan. 20, 2016, which claims priority of European Patent Application Number 15151794.3, filed on Jan. 20, 2015.

BACKGROUND

Various common diseases of the cardiovascular system like venous and arterial thrombosis, pulmonary embolism, myocardial infarction and related unstable angina are currently treated with parenteral administration of unfractionated heparin (UFH) or its lower molecular weight analogous (LMWH) in clinics.[1] Despite the development of more conveniently administered oral anticoagulants subcutaneously injected heparin is still the benchmark anticoagulant in prophylaxis of patients with risk of venous thromboembolism after surgery. However, after several decades of successful clinical use of UFH and LMWH as parenteral anticoagulants during surgical procedures as well as prophylaxis of thrombotic complications, bleeding still remains one of the major complications.[2] In addition, the fact that both UFH and LMWHs are derived from animal tissues raises concerns over their safety as it could lead to severe risk of disease transmission.[3]

Heparin is a naturally occurring, partially O- and N-sulfated linear polysaccharide with broad structural variability. It belongs to the class of glycosaminoglycans consisting of an alternating sequence of D-glucosamine and uronic acids. It is commonly isolated from mucosa of porcine intestine, but is also naturally found in lung and liver tissue. Its natural dispersity is broad and molecular weights of the isolated material range from around 4 to 30 kDa with an abundance maximum at 15 kDa. Lower molecular weight heparins (LMWHs) refer to the same composition and structural variability but are of lower molecular weight. Such LMWHs are refined from UFH by chemical or enzymatic degradation which yields, e.g. Enoxaparin (4.5 kDa) or Tinzaparin (6.5 kDa) with lower polydispersity compared to UFH. FIG. 1 illustrates the polydispersity and molecular weight range in daltons of commonly applied UFH and LMWH. The graph is taken from reference [1]. The respective molecular weight and dispersity characteristic of heparin determines its mode of action as an anticoagulant as well as its bioavailability and pharmacokinetics (vide infra).

Recently, adverse immunogenic reactions due to antibody development against heparins have been observed in patients after heparin administration that can lead to life threatening heparin induced thrombocytopenia (HIT).[4] HIT is characterized by a sudden drop of platelet counts in patients, usually between day 5 and day 13 after the first heparin administration and leads to an increased propensity to thrombosis. It is known, that the electrostatic interaction and binding of heparin to platelet factor 4 ($PF_4$) in plasma induces a conformational change of $PF_4$ which now exposes an epitope that can be recognized by platelet-activating antibodies of the immunoglobulin G class. A minimum of 12-14 saccharide units are required to form such antigenic multi-molecular heparin/$PF_4$ complexes. Therefore, patients with LMWH treatment are less prone to but not safe from HIT development. The ionic complex formation between anionic heparins and positively charged $PF_4$, however, is independent of the composition of the polysulfate since it was shown that non-carbohydrate based anionic, linear polymers can also form complexes with $PF_4$, given the chain length is long enough, thus the molecular weight is high enough, to span the tetrameric $PF_4$ protein.[5] Another unwanted side effect of heparin is osteopenia which is caused by heparin binding to osteoblast cells and results in the release of osteoclast activating factors which in turn causes lowering of bone mineral density.[6]

Especially in such cases of acute, unexpected side effects or also when unintendedly overdosed an antidote for the anticoagulant drug is required. Protamine sulfate, a highly cationic peptide that binds and neutralizes the anionic charges of UFH and LMWHs, and completely reverses the action of UFH and partially reverses the anticoagulant activity of LMWHs. [7]

Due to the huge structural inhomogeneities of heparin including broad molecular weight distribution, the biological and anticoagulant activity of each batch of heparin is unpredictable and different. For standardization the activity of UFH or LMWH is usually given in international units with respect to their activated Factor X (FXa) inhibition. In general, only 30% of the mass fraction of heparin has a strong anticoagulant effect the remaining 60% are biologically inactive in terms of anticoagulation. In addition, the response of each patient towards intravenous (i.v.) heparin administration can be very different, does not show a linear dose response and thus requires constant monitoring in hospital and readjustment of dose during heparin therapy in order to reduce the risk of bleeding. Typically, the activated partial thromboplastin time (aPTT), an in vitro blood coagulation assay with fresh, citrated platelet poor plasma (PPP) of the patient is used in hospitals to monitor and evaluate efficacy of the therapy.

The low molecular weight fraction of heparin binds to circulating antithrombin III (ATIII) with high affinity in the blood stream and thereby causes a conformational, irreversible change in ATIII. ATIII is a natural inhibitor of the two major coagulation enzymes, Factor Xa (FXa) and thrombin (Factor IIa (FIIa)) that circulate in blood. Binding of heparin to ATIII potentiates the affinity of antithrombin for thrombin and FXa due to the induced conformational change in ATIII and yields an up to 1000 times faster binding/inhibition of the enzymes via ternary complex formation. The corresponding reaction schemes are depicted in FIGS. 2A to 2C that show the mode of action of UFH (A), LMWH (B) and the ATIII specific pentasaccharide unit of UFH (C) in ATIII mediated thrombin (FIIa) and FXa inhibition. These Figures are taken from reference [8].

As illustrated in FIG. 2A a minimum chain length of 18 saccharide units of the anticoagulant (as present in UFH) is required in order to efficiently inhibit thrombin since the ATIII specific pentasaccharide unit binds to ATIII with high affinity and induces the conformational change while the remaining 13 units bind to an exosite on thrombin to bridge and stabilize the formed ternary complex (FIG. 2A).[2] Via a similar ternary complex FXa is inhibited by UFH, however, no additional binding of UFH to FXa is required for efficient inhibition. Thus, the preferred inhibition pathway of shorter chain LMWHs within the coagulation cascade is ATIII mediated FXa binding rather than indirect FIIa binding (FIG. 2B). Often the chain length of LMWH is too short in order to form the ternary LMWH/ATIII/FIIa complex. Consequently, the ATIII specific pentasaccharide unit of UFH, is exclusively able to inhibit FXa as illustrated in FIG. 2 C). FIGS. 2A to 2C correspond to according Figures of reference [8].

The pharmacokinetics of UFH are complex mainly due to the structural inhomogeneity of the sulfated polysaccharide and show significant difference from LMWH. Also the specific activity in terms of anticoagulation varies significantly for both and yields unpredictable and non-linear dose response in patients. When administered intravenously UFH and its derivatives immediately bind to several plasma proteins (not only ATIII), the endothelium, platelets or macrophages due to their high negative charge density, which drastically reduces their bioavailability. Thereby UFH shows higher affinity for plasma proteins and cellular blood components than LMWH. After cellular binding heparin becomes internalized into the cells where it is depolymerized. This event is commonly attributed to the rapid saturation phase of clearance. Once the cellular binding sites are saturated, heparin circulates systemically and is cleared more slowly via the kidneys. The non-linear response of UFH after i.v. administration at therapeutic dose is obvious via the observed half lives of 30, 60, and 150 minutes with a bolus of 25, 100, and 400 U/kg, respectively. [9] The pharmacokinetics of LMWHs is superior to the one of UFH since the shorter chains bind less efficiently to plasma proteins and to the endothelium and hence have longer half-lives in plasma and a more linear dose response compared to UFH. Clearance mainly occurs renal and is only an issue for patients with renal disorders. However, protamine sulfate as the only approved and commonly used antidote for UFH is not 100% effective for LMWHs which thus leads to a non-complete reversal of the anticoagulant properties of LMWHs with protamine sulfate as compared to UFH.

A safer and clinically more predictable alternative to UFH and LMWH is fondaparinux, a fully synthetic pentasaccharide drug with high negative charge density. Fondaparinux is an analog of the minimum structural pentasaccharide fraction of heparin for efficient binding to ATIII which exhibits the most linear and predictable dose response among the three mentioned sulfated polysaccharide anticoagulants with a half-life of 17 h after subcutaneous administration. However, fondaparinux is only available via tedious multistep synthesis which makes it cost intensive. In addition, the drug suffers from the lack of an effective clinical antidote as compared to UFH and LMWHs.

Hence, to overcome limitations of current indirect, ATIII mediated anticoagulants the demand for new, more defined, and safer alternatives is emerging. In pursuit of such alternatives, direct thrombin inhibitors such as FDA approved hirudin and argratroban have been developed which, however, are still associated with certain risk of bleeding.[10] Aptamers, small nucleic acid molecules, in contrast, also work as direct inhibitors but are not yet approved. They seem to have no risk of associated bleeding, low immunogenicity, show predictable dose response, adjustable pharmacokinetics, and have an effective antidote available.[11] High production costs remain a disadvantageous fact.

Many other polysulfated or polyanionic polymers have been identified as polymers with anticoagulant properties via in vitro coagulation assays (e.g. aPTT) with platelet poor plasma (PPP).[12] Only a few of them, however, have been proven to work in whole blood as well, e.g. via thromboelastography in vitro, which can measure the time dependent built up and break down of a blood clot in whole blood simultaneously with clot strength. Especially biocompatibility of such polymers including complement activation and cell toxicity is an issue for safe use in vivo.

Besides the therapeutic or prophylactic use of anticoagulants in clinics, there is also a demand for the modification of medical devices which come in contact with blood such as blood bags, blood collection vials, blood based diagnostic assay surfaces and others. Material surface induced thrombus generation is a major clinical concern associated with medical devices such as coronary stents, heart valves, catheters, vascular grafts, extracorporeal tubing, hemodialysis membranes and glucose sensors. The contact activation pathway of the blood coagulation cascade is thought to be involved in the initiation of such events. In order to prevent material surface induced activation of the coagulation pathway and hence thrombus formation catheters are currently routinely pretreated (washed) with heparin solution. By this noncovalent procedure the intended anti-coagulant layer on the surface is not stable and flushed away easily and therefore heparin can unintendedly enter into the bloodstream and affect blood coagulation.

As mentioned above the key enzyme involved in the activation of blood coagulation is thrombin. Hence, approaches to minimize thrombin generation on the surface is an effective way to reduce surface initiated thrombus formation. The covalent surface attachment of heparin has been proven useful and is currently used in many medical devices. However, immobilized heparin's activity is believed to be dependent on the method of covalent surface attachment. With this respect significant issues still exist. Heparin activity is highly diminished by the current immobilization approaches and end-functionalization of heparin without loss of activity is not trivial. Thus new surface modification approaches to generate anti-thrombotic surfaces will revolutionize in particular vascular implant/device industry.

In 2004 Haag et al. synthesized dendritic polyglycerol sulfate for the first time and studied its effect on in vitro blood coagulation and complement activation.[13] Non-sulfated dendritic polyglycerol as the precursor for the latter compound is a highly bio- and haemocompatible, water soluble polymer.[14-17] The same applies to linear polyglycerol.[17-19] Upon sulfation of the multiple hydroxyl groups which are located on the periphery of the dendritic polymer the resulting polyglycerol sulfate (dPGS) exhibits 30% of the anticoagulant activity of UFH in PPP via aPTT in vitro.[13] In addition, dPGS was found to be non-activating for complement in this study via a blood based in vitro assay. In 2008, dPGS was shown by Haag and coworkers to be highly effective in inflammatory settings via L- and P-selectin inhibition in vivo and well tolerated by mice up to an i.v. bolus of 10 to 30 mg/kg.[20-21]

Zhongyu Li and Ying Chang: "Synthesis of Linear Polyether Polyol Derivatives As New Materials for Bioconjugation", Bioconjugate Chem. 20 (2009), pages 780-789 describes linear polyether polyol derivatives that can carry different substituents, amongst them carboxyl groups or tosylate groups. This publication describes in addition different methods of manufacturing such compounds. One such method is a Williamson reaction in which a linear polyether polyol compound is converted with 2-chloroacetic acid so as to obtain carboxymethyl polyether polyol.

Jens Kölller et al.: "Post-polymerization functionalization of linear polyglycidol with diethyl vinylphosphonate", Chem. Commun. 47 (2011), pages 8148-8150 describes a partial phosphonatization of a linear polyglycidol with diethyl vinylphosphonate in a Michael-type reaction. The resulting compound is—after saponification—a linear polyglycidol carrying a phosphonate group.

WO 2008/015015 A2 describes dendritic polyglycerol sulfonates.

SUMMARY

It is an object of the instantly claimed invention to provide a compound that has a higher anti-coagulant activity than dendritic polyglycerol sulfate (dPGS) has and to provide uses of such a compound and a method of manufacturing such a compound.

This object is achieved by a linear and optionally terminally substituted polyglycerol compound comprising a backbone of linearly linked glycerol residues. This linear polyglycerol compound carries a plurality of substituents in the nature of covalently bound negatively charged sulfates. Thereby, a degree of substitution of the backbone is between 10 and 100% (including the upper and lower limit).

Sulfates as negatively charged groups have specific effects over other negatively charged groups. These effects will be explained in connection with FIG. 17.

Nonetheless, in an alternative of the instantly claimed subject-matter, the negatively charged groups are chosen from the group consisting of sulfates, sulfonates, phosphates, phosphonates, bisphosphonates and carboxylates as well as combinations or mixtures thereof. This alternative is part of the instant disclosure. The subsequently explained embodiments can be also be applied to this alternative.

Since at least some of the hydroxyl groups of the backbone of the linear polyglycerol compound are substituted by negatively charged groups, the compound can also be denoted as substituted linear polyglycerol or as anionic substituted linear polyglycerol. More specifically, in case of sulfates as negatively charged groups, the substituted linear polyglycerol can be denoted as linear polyglycerol sulfate (lPGS).

In an embodiment, that the degree of substitution of the backbone is between 15% and 95%, in particular between 20% and 90%, in particular between 25% and 85%, in particular between 30% and 80%, in particular between 35% and 75%, in particular between 40% and 70%, in particular between 45% and 65%, in particular between 50% and 60%, in particular between 55% and 58%, (in each case including the upper and lower limits). A very well suited degree of substitution is between 50% and 100%. Another very well suited degree of substitution is between 70% and 100%. Another very well suited degree of substitution is between 85% and 100%. Another very well suited degree of substitution is between 90% and 100% (in each case including the upper and lower limit).

In an embodiment, the median carbon atom of a first glycerol unit in the linear polyglycerol compound (C2 atom) is linked to one of the two terminal carbon atoms in a second glycerol unit (C1 atom) via an ether. Thereby, a 1,2-linkage between adjacent glycerol units in the linear polyglycerol compound is formed. It can also be denoted as 2,1-linkage. In an embodiment, the terminal carbon atom of a first glycerol unit in the linear polyglycerol compound (C1 or C3 atom) is linked to one of the two terminal carbon atoms in a second glycerol unit (C1 or C3 atom) via an ether. Thereby, a 1,3-linkage between adjacent glycerol units in the linear polyglycerol compound is formed. It can also be denoted as 3,1-linkage. In an embodiment, the individual glycerol units of the claimed compound are either exclusively 1,2-linked to each other or exclusively 1,3-linked to each other.

The general formulae of such 1,2-linked and 1,3-linked polyglycerol compounds are depicted below, wherein the meanings of the indicated residues in an embodiment are also indicated:

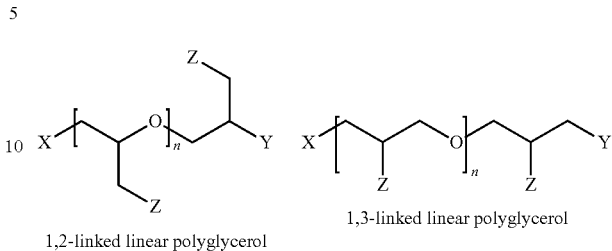

1,2-linked linear polyglycerol     1,3-linked linear polyglycerol with
n=5 to 1000,
X, Y=independently from each other any organic residue with a functional group chosen from the group consisting of alcohol, amine, thiol, azide, alkyne, alkene, carboxylic acid, aldehyde, ketone, halogen, isocyanate, isothiocyanate, Michael acceptor/donor group,
Z=independently from other residues Z in the same polyglycerol molecule any negatively charged residue in the nature of a sulfate,
  or an unreacted neutral precursor residue bearing a reactive of an alcohol, amine, thiol, halogen, azide, alkyne, alkene, carboxylic acid, or Michael acceptor/donor group,
  wherein at least 30% of all residues Z in the polyglycerol bear a negative charge.

I.e., it is possible that all residues Z are a mixture of negatively charged residues and unreacted neutral precursor residues, wherein anionic charges have a percentage of at least 30%.

In an alternative to the instantly claimed subject-matter, residue Z can additionally have the meanings sulfonate, phosphate, phosphonate, bisphosphonate, and carboxylate. Thereby, the carboxylate is that is linked to the polyglycerol backbone via ester, triazole, thioether, ether, urea, carbamate, imine, amide, imide, disulfide, or similar linkers. This alternative is part of the instant disclosure. The subsequently explained embodiments can be also be applied to this alternative.

In an embodiment, the backbone has a number average molecular weight ($M_n$) of 1 kDa to 100 000 kDa, in particular of 2 kDa to 90 000 kDa, in particular of 3 kDa to 80 000 kDa, in particular of 4 kDa to 70 000 kDa, in particular of 5 kDa to 60 000 kDa, in particular of 6 kDa to 50 000 kDa, in particular of 7 kDa to 40 000 kDa, in particular of 8 kDa to 30 000 kDa, in particular of 9 kDa to 20 000 kDa, in particular of 10 kDa to 10 000 kDa, in particular of 11 kDa to 5 000 kDa, in particular of 12 kDa to 1 000 kDa, in particular of 13 kDa to 750 kDa, in particular of 14 kDa to 500 kDa, in particular of 15 kDa to 400 kDa, in particular of 16 kDa to 300 kDa, in particular of 17 kDa to 200 kDa, in particular of 18 kDa to 100 kDa, in particular of 19 kDa to 90 kDa, in particular of 20 kDa to 80 kDa, in particular of 21 kDa to 70 kDa, in particular of 22 kDa to 60 kDa, in particular of 23 kDa to 50 kDa, in particular of 24 kDa to 40 kDa, in particular of 25 kDa to 30 kDa. Ranges of 2 kDa to 480 kDa, in particular of 2 kDa to 250 kDa, in particular of 2 kDa to 120 kDa, in particular of 2 kDa to 54 kDa, in particular of 1 kDa to 25 kDa are particularly well suited. Thereby, a combination with a degree of substitution of 70% to 100% is particularly well suited.

Particularly suited number average molecular weight (Mn) ranges of the backbone are 2 kDa to 6 kDa, in particular 2.5 kDa to 5.5 kDa, in particular 3 kDa to 5 kDa (in each case including the upper and lower limits). Particularly suited degrees of sulfation, especially to be used in combination with the before-mentioned particularly suited Mn ranges are between 50% and 100%, between 70% and 100%, between 85% to 100%, and in particular between 90% to 100%.

In an embodiment, the before-mentioned number average molecular weight ranges and degrees of sulfation are combined so as to result, e.g., in a linear polyglycerol compound having a number average molecular weight (Mn) of 2 kDa to 6 kDa and a degree of sulfation of 50% to 100%, in particular a number average molecular weight (Mn) of 2 kDa to 6 kDa and a degree of sulfation of 70% to 100%, in particular a number average molecular weight (Mn) of 2 kDa to 6 kDa and a degree of sulfation of 85% to 100%, in particular a number average molecular weight (Mn) of 2 kDa to 6 kDa and a degree of sulfation of 90% to 100%, in particular a number average molecular weight (Mn) of 2.5 kDa to 5.5 kDa and a degree of sulfation of 50% to 100%, in particular a number average molecular weight (Mn) of 2.5 kDa to 5.5 kDa and a degree of sulfation of 70% to 100%, in particular a number average molecular weight (Mn) of 2.5 kDa to 5.5 kDa and a degree of sulfation of 85% to 100%, in particular a number average molecular weight (Mn) of 2.5 kDa to 5.5 kDa and a degree of sulfation of 90% to 100%, in particular a number average molecular weight (Mn) of 3 kDa to 5 kDa and a degree of sulfation of 50% to 100%, in particular a number average molecular weight (Mn) of 3 kDa to 5 kDa and a degree of sulfation of 70% to 100%, in particular a number average molecular weight (Mn) of 3 kDa to 5 kDa and a degree of sulfation of 85% to 100%, in particular a number average molecular weight (Mn) of 3 kDa to 6 kDa and a degree of sulfation of 90% to 100%.

Compounds having the before-mentioned number average molecular weights and degrees of sulfation are particularly suited for in vivo applications.

In an embodiment, the linear polyglycerol compound is end functionalized with a functional group chosen from the group consisting of azide, bromide, chloride, iodide, fluoride, primary amine, secondary amine, tertiary amine, carboxylic acids, thiols, disulfides, ketals, acetals, aldehydes, and of hydroxyl, isocyanate, isothiocyanate, unsaturated carbon-carbon units having double or triple bonds, a Michael acceptor (such as an $\alpha,\beta$-unsaturated aldehyde, ketone, ester, carboxylic acid amide, carboxylic acid imide, such as maleimide, or an $\alpha,\beta$-unsaturated nitrile) and a Michael donor (such as organic copper compounds, amines, thiols, phenolate ions, cyanides and acrylates). I.e., at least one terminus of the polyglycerol compound carries an according reactive group in this embodiment.

In an embodiment, the linear polyglycerol compound is bound to a surface of an article. Thus, the compound is suited for surface modification and thus enables the manufacturing of articles having specific properties mediated by the linear polyglycerol compound. In an embodiment, the linkage to the surface is a covalent linkage. Thereby, the linear polyglycerol compound can form a layer on the surface of the article. It is thus possible to enable a linkage between the surface modified article and certain proteins that have a binding site which is able to bind the linear polyglycerol compound. E.g., a heparin binding site is a suited binding site, in particular if the substituents of the linear polyglycerol compound are sulfates.

End-functionalized linear polyglycerol compound (such as lPGS) are easily accessible and can be used for surface modification of implants (catheters, leads, vascular devices, hemodialysers, heart-pumps etc.) in order to provide unique antithrombotic surfaces. Other areas for application of surface conjugated linear polyglycerol compounds include, but are not limited to, tissue engineering and drug delivery (e.g., growth factor delivery). Thus, the linear polyglycerol compound has the unique potential to address current unmet clinical needs in anticoagulation therapy, in the development of blood compatible, anti-thrombotic surfaces and in regenerative medicine.

In an embodiment, the described linear polyglycerol compound is used as a medicament. Suited areas of application are conventional anticoagulation therapy, prophylactic treatments of venous and arterial thrombosis and cancer. Thus, the instant invention relates to method of treating a human or an animal (in particular a non-human mammal) in need thereof with a medicament comprising a linear polyglycerol compound according to the preceding explanations.

In an embodiment, the linear polyglycerol compound is used as an anti-coagulant. Thus, the instant invention relates to method of treating a human or an animal (in particular a non-human mammal) in need thereof with an anti-coagulant comprising a linear polyglycerol compound according to the preceding explanations. Suited areas of application are named above. In addition, in vitro applications comprise utilization of lPGS, e.g., in blood collection tubes used in medical clinics, hospitals and blood banks.

The instantly claimed invention relates in an aspect also to a method for manufacturing a linear polyglycerol compound according to the preceding explanations. Thereby, the method comprises the following steps
 a) providing a linear polyglycerol compound, comprising a backbone of linearly linked glycerol residues bearing hydroxyl groups or other functional groups chosen from the group consisting of azides, alkynes, alkenes, thiols, halogens, primary or secondary amines, isocyanates, isothiocyanates, carboxylic acids, aldehydes, ketons and any Michael donor or acceptor for conjugation of anionically charged entities, and
 b) causing a reaction of at least some of these hydroxyl groups or these other functional groups of the linear polyglycerol compound provided in step a) with a compound introducing a negatively charged group into the linear polyglycerol compound, this compound being at least one chosen from the group consisting of sulfuric acid, sulfonic acid, a sulfuric acid derivative, and a sulfonic acid derivative.

In an alternative of the instantly claimed subject-matter, the compound introducing a negatively charged group is at least one chosen from the group consisting of sulfuric acid, sulfonic acid, phosphoric acid, phosphonic acid, bisphosphonic acid, and any kind of carboxylic acid. This alternative is part of the instant disclosure. The subsequently explained embodiments can be also be applied to this alternative.

The anion generating reagents (i.e. the compounds introducing a negatively charged group into the linear polyglycerol compound, in particular a sulfuric acid, a sulfonic acid, a sulfuric acid derivative, and a sulfonic acid derivative) are typically acid derivatives such as acids in an activated form such as acid chlorides, e.g., chlorosulfonic acid or sulfurochloridic acid, their respective (stabilized) acid anhydrides, e.g., stabilized sulfur trioxide complex and sulfamic acid, their respective reactive salts or cleavable esters. Pyridinium p-toluenesulfonate is a suited anion generating agent. In certain cases also cyclic reagents like sulfones, phospholanes, dioxathiolane dioxides or lactones can be applied in order to introduce anionically charged groups. In cases where the anionic groups are introduced by activated acids or their respective cleavable esters the acidic proton (after ester cleavage) is exchanged with a mono or bivalent counter cation or mixtures thereof, e.g. $Li^+$, $Na^+$, $K^+$, $NH_4^+$, $Mg^{2+}$, $Ca^{2+}$ or others typically by a common acid base reaction.

The claimed invention relates in an aspect also to a gel that comprises a plurality of linear polyglycerol compounds according to the preceding explanations as well as a crosslinker and optionally a copolymerization compound. Thereby, statistically each crosslinker molecule is covalently bound to one or more molecules of the linear polyglycerol compound. Each crosslinker molecule has more than two (e.g. 3, 4, 5) reactive groups. Such a gel can be applied on device/implant surfaces.

In an embodiment, statistically each crosslinker molecule is covalently bound to more than two molecules of the linear polyglycerol compound. For this purpose, each crosslinker molecule has more than two (e.g. 3, 4, 5) reactive groups, and each linear polyglycerol compound molecule bears two reactive groups (one on each of its termini). Thus, each crosslinker can link at least 2 linear polyglycerol compound molecules together and can additionally introduce branchings into a network of polyglycerol compound molecules by additionally linking a third linear polyglycerol compound molecule. It is not necessary that every crosslinker molecule is bound to three linear polyglycerol compound molecules. Rather, a stable gel can also be built up if only some of the crosslinker molecules are bound to three linear polyglycerol compound molecules and if the other crosslinker molecules are bound to one, two or more linear polyglycerol compound molecules.

A gel according to the preceding explanations can be used for storing at least one compound in vitro or in vivo. A suited compound is a pharmaceutically active compound. Peptides, nucleic acids (such as miRNAs) or proteins may be used as compound (regardless of being pharmaceutically active or not) A suited protein is a growth factor. It can be used for cell culturing purposes by growing cells on such a gel and supplementing the cells with proteins stored in the gel. Another well suited area of application of such gels is tissue engineering. Such a gel can also be used as carrier for delivering compounds in vitro or in vivo.

The invention relates in an aspect to a method of storing at least one protein in vitro or in vivo by mixing said protein with a gel according to the preceding explanations and thus embedding the protein in the gel. The invention relates in a further aspect to a method for growing cells in vitro by letting the cells grow on a gel that is optionally supplemented by at least one protein. The invention relates in a further aspect to a method for tissue engineering by using such a gel as matrix for the tissue to be grown or cultivated on. The invention relates in a further aspect to a method for delivering proteins in vitro to cells or in vivo to a human or animal (in particular a non-human mammal) in need thereof.

Kizhakkedathu et al. designed, developed, and investigated a so called universal heparin binding polymer as an in vivo effective universal antidote for UFH, LMWH, fondaparinux and other heparinoids.[22]

The instant inventors could surprisingly show that this universal heparin binding polymer (UHBP) is also suited as antidote for the linear polyglycerol compound as described above, in particular for a polyglycerol sulfate as explained above. Therefore, the instant invention relates in aspect to the use of UHBP as antidote for the linear polyglycerol compound, in particular if the compound carries sulfate groups as negatively charged groups. The invention relates in another aspect to a method for deactivating (or for neutralizing the activity of) the linear polyglycerol compound by causing a binding to UHBP (e.g. by adding UHBP to a culture or an organism in which or whom the linear polyglycerol compound is present).

All embodiments of the described linear polyglycerol compound, its use and the disclosed methods can be combined in any desired way and are transferable to any other category of subject-matter that is herein disclosed (i.e. from the compound to a method or from a method to a use or from a use to a method etc.).

BRIEF DESCRIPTION OF THE DRAWINGS

Aspects of the invention will now be explained in more detail by examples and accompanying figures.

FIG. 3 shows a typical synthesis scheme for lPGS.

DETAILED DESCRIPTION

Figure 1:
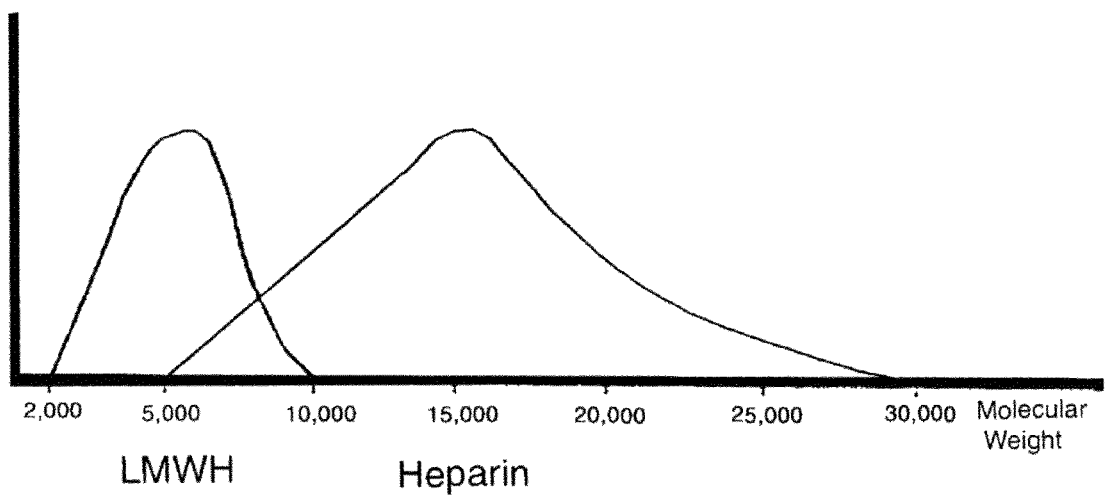
FIG. 1 shows the molecular weight distribution of UFH and LMWH in daltons.
Figure 2A:
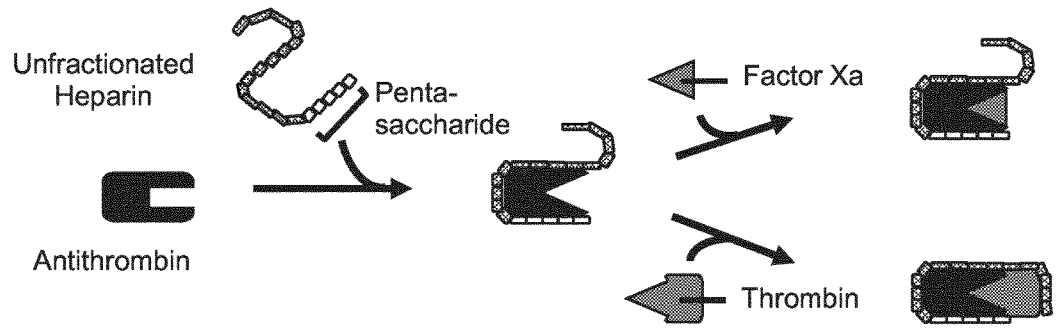
FIG. 2 shows the mode of action of UFH (A), LMWH (B) and the ATIII specific pentasaccharide unit of UFH (C) in ATIII mediated thrombin (FIIa) and FXa inhibition.
Figure 2B:
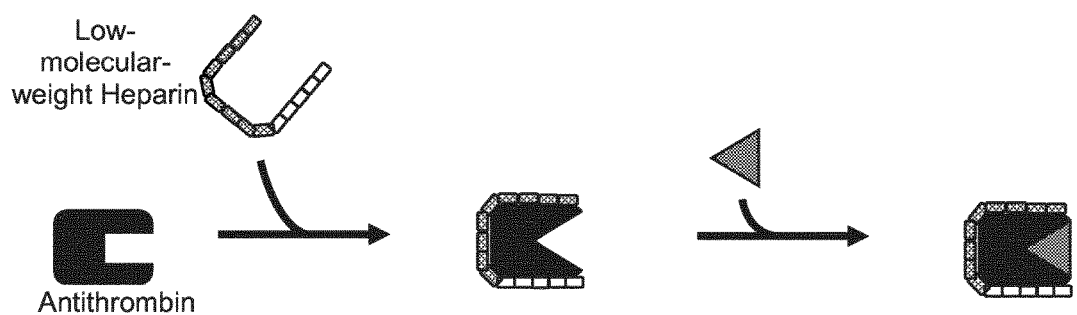
Figure 2C:
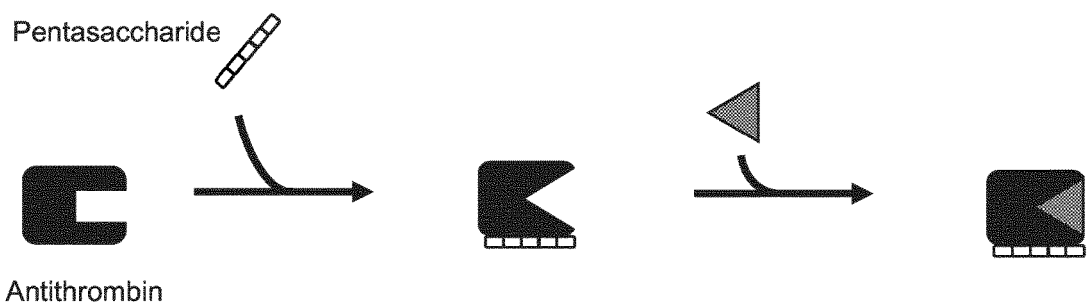

So far unpublished data of the inventors indicated that there is no difference between dPGS and lPGS in their anti-inflammatory potential. However, there was an unexpected and significant difference of dPGS and lPGS in terms of their anti-coagulant effect on blood in vitro. Within the following section an aspect of the invention relating to lPGS as a specific linear polyglycerol compound will be explained in detail.

LPGS is a fully synthetic, structurally defined, non-carbohydrate based polymer. It can be used for anti-coagulant therapy. The lPGS molecules showed surprisingly potent anticoagulant activity similar to unfractionated heparins (UFH) and low molecular weight heparins (LMWH). Unlike heparins they are fully synthetic and homogenous in structure. The in vivo activity and circulation time of lPGS can be adjusted and fine-tuned by the molecular weight which in turn can be precisely controlled via the underlaying anionic polymerization mechanism. Due to their synthetic nature, there will not be any fear of biological contamination (such as contamination by bacteria, viruses, immunomodulatory carbohydrates etc.).

LPGS is defined as a linear polyether based on a linear polyglycerol backbone which can be synthesized with adjustable molecular weight via controlled anionic polymerization of e.g., a side chain acetal protected glycerol monomer such as ethoxyethyl gycidyl ether (EEGE).[17-18, 23-24] Achieved polydispersities are typically below 1.3 and often lower than 1.1. Control over the end group of the synthesized polymer can be achieved via the applied initiator of the polymerization.[25] In addition, the acetal protecting groups in the side chain of the obtained polymer (PEEGE) allow selective post-functionalization of the terminal hydroxyl functionality. Acidic treatment and hydrolysis of the polymer's acetal side chains generates end group functionalized linear polyglycerol (lPG). Sulfation via e.g. sulfur trioxide pyridine complex yields linear polyglycerol sulfate (lPGS) with adjustable degree of sulfation (DS) analogously to dPGS.

A suited synthesis sequence for terminally monobromo or monoazido functionalized lPGS is outlined in FIG. 3 which show a suited synthetic scheme for lPGS using monomer activated anionic polymerization of EEGE to PEEGE, acidic hydrolysis to lPG and subsequent sulfation to yield lPGS. Functional or reactive terminal groups are introduced via application of the respective tetraalkyl ammonium salt during polymerization, e.g., to yield terminal monobromo functionalized polymers (A) or terminal monoazido functionalized polymers for use in surface modification (B) (cf. also FIG. 16). Control over the functional end-group of the polymer is simply achieved by applying the respective tetraalkylammonium salt as an initiator of the anionic polymerization. Terminal monoazide functionalized lPGS can immediately be applied for azide/alkyne click chemistry surface immobilization or for surface immobilization by suitable linkers for the generation of anti-thrombotic surfaces (cf. FIG. 16).

Analytical specifications in terms of molecular weight and polydispersity index (PDI) of synthesized lPGS samples determined via gel permeation chromatography multi-angle light scattering (GPC-MALLS) of their respective lPG backbones and degrees of sulfation, determined via $^1$H NMR and combustion analysis, are summarized in Table 1. Nomenclature of lPGS and dPGS samples is as such that the molecular weight (MW) of the lPG backbone or dPG core is given in kDa in subscripts after PG and the number of sulfate groups is given in subscripts after S. Accordingly, a sample $lPG_{5kDa}S_{45}$ encodes a lPGS polymer with a lPG backbone of 5 kDa and 45 sulfate groups per molecule which equals a degree of sulfation of DS=67%.

TABLE 1

Analytical specification of lPGS and dPGS samples as well as commercial UFH and Tinzaparin as control samples for biological evaluation.

| Sample name | $M_n$ of l/dPG backbone/core | PDI | $M_n$ of sample | number of sulfate groups per polymer | DS in % |
|---|---|---|---|---|---|
| $lPG_{2\,kDa}S_{17}$ | 1.9 | 1.15 | 3.6 | 17 | 63 |
| $dPG_{2\,kDa}S_{27}$ | 2.0 | 1.60 | 4.7 | 27 | 100 |
| $lPG_{3\,kDa}S_{44}$ | 3.2 | 1.09 | 7.7 | 44 | 100 |
| $dPG_{3\,kDa}S_{6}$ | 3.0 | 1.60 | 3.6 | 6 | 15 |
| $dPG_{3\,kDa}S_{12}$ | 3.0 | 1.60 | 4.2 | 12 | 30 |
| $dPG_{3\,kDa}S_{38}$ | 3.0 | 1.60 | 6.7 | 38 | 94 |
| $lPG_{5\,kDa}S_{0}$ | 5.0 | 1.07 | 5.0 | 0 | 0 |
| $lPG_{5\,kDa}S_{19}$ | 5.0 | 1.07 | 7.2 | 19 | 28 |
| $lPG_{5\,kDa}S_{36}$ | 5.0 | 1.07 | 9.3 | 36 | 54 |
| $lPG_{5\,kDa}S_{60}$ | 5.0 | 1.07 | 12.1 | 60 | 90 |
| $dPG_{5\,kDa}S_{64}$ | 5.0 | 1.60 | 11.5 | 65 | 100 |
| $dPG_{6\,kDa}S_{65}$ | 6.0 | 1.60 | 12.5 | 64 | 80 |
| $lPG_{10\,kDa}S_{135}$ | 10 | 1.09 | 25.9 | 135 | 100 |
| $lPG_{25\,kDa}S_{94}$ | 25 | 1.11 | 36.1 | 94 | 28 |
| $lPG_{25\,kDa}S_{162}$ | 25 | 1.11 | 44.1 | 162 | 48 |
| $lPG_{25\,kDa}S_{337}$ | 25 | 1.11 | 64.8 | 337 | 100 |
| $dPG_{25\,kDa}S_{88}$ | 25 | 1.33 | 34.0 | 88 | 26 |
| $dPG_{25\,kDa}S_{145}$ | 25 | 1.33 | 39.8 | 145 | 43 |
| $dPG_{25\,kDa}S_{306}$ | 25 | 1.33 | 56.2 | 306 | 91 |
| $lPG_{54\,kDa}S_{625}$ | 54 | 1.31 | 118 | 625 | 85 |
| $dPG_{120\,kDa}S_{1264}$ | 120 | 1.60 | 249 | 1264 | 78 |
| $dPG_{250\,kDa}S_{2667}$ | 250 | 1.60 | 522 | 2667 | 79 |
| $dPG_{480\,kDa}S_{5185}$ | 480 | 1.60 | 1009 | 5185 | 80 |
| UFH | n.a. | 1.3-1.4* | 12-16* | | |
| Tinzaparin | n.a. | — | 6.5* | | | n.a. not applicable,
*data taken from literature[26]

Figure 4:
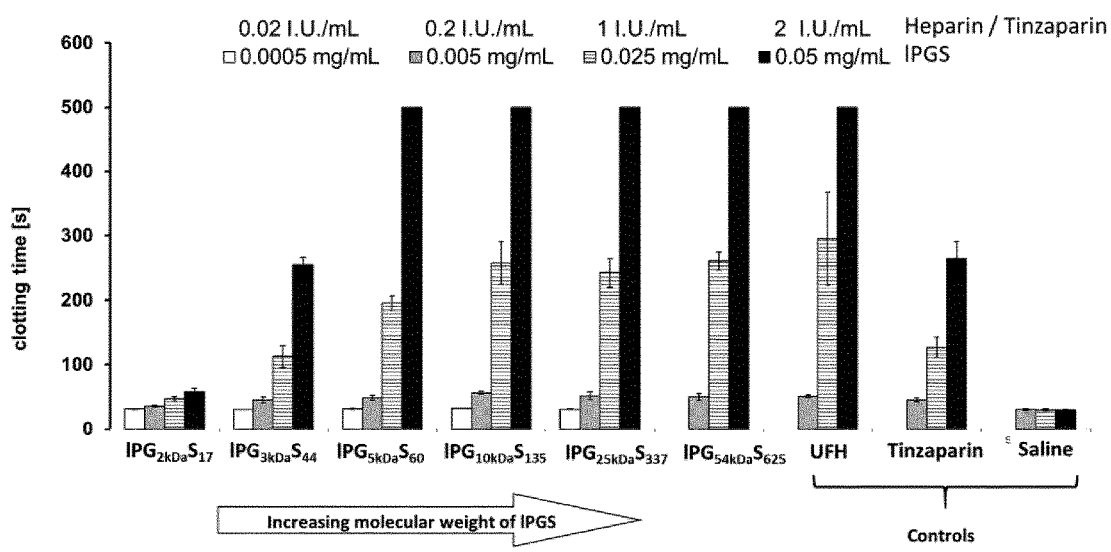
FIG. 4 shows concentration dependent aPPT plasma clotting times with lPGS of different molecular weight backbone.

Within a first screening of the anticoagulant efficiency, the polysulfates were evaluated in an in vitro activated partial thromboplastin time (aPTT) coagulation assay using fresh human platelet poor plasma (PPP) from healthy, consented donors. Via aPTT the intrinsic and common pathway of blood coagulation are tested with PPP which is the standard in vitro assay to monitor patients on heparin therapy. Blood samples were collected in citrated vacutainer tubes from BD (9:1 v/v blood to buffered sodium citrate solution) in order to prevent contact activated coagulation. Sodium citrate complexes $Ca^{2+}$ ions in the blood sample which are mandatory for coagulation enzymes to work. Thus, coagulation is hindered in the presence of sodium citrate when no free calcium ions are available. The anticoagulant effect of sodium citrate can easily be reversed by addition of more calcium ions, e.g., added as calcium chloride solution, in order to saturate the calcium complexing sites of citrate and provide free uncomplexed calcium ions for the coagulation enzymes. After blood collection the samples are centrifuged (20 minutes, 1200×g) at room temperature in order to separate cellular components of blood including platelets from plasma. The obtained clear yellow upper phase (PPP) in the tube after centrifugation is separated and used immediately for the aPTT assay applying a ST4 automated hemostasis coagulation analyzer (Diagnostic Stago, Inc.) with mechanical endpoint determination. Therefore, PPP (180 μl) was mixed with polysulfate stock solutions (20 μl) in saline of various concentration at room temperature. Then the anticoagulated plasma was mixed with the partial thromboplastin reagent (Actin®FSL from Dade Behring) in a 1:1 ratio (200 μl each), 100 μl of this mixture was transferred into a well of cuvette strips, respectively and incubated for three minutes at 37° C. Subsequently, coagulation was initiated by addition of prewarmed (37° C.) calcium chloride solution (0.025 mM, 50 μl) into each well and time was recorded until a fibrin clot was formed at 37° C. Coagulation times of the polyglycerol sulfates were evaluated in comparison with saline treated PPP (untreated control) as well as UFH or Tinzaparin, a clinically used LMWH, treated PPP. Concentration dependent clotting times (in seconds) from at least three repeat experiments are graphically illustrated in FIG. 4. Specifically, FIG. 4 shows concentration dependent aPPT plasma clotting times with lPGS of different molecular weight backbones and high degree of sulfation, respectively. UFH and Tinzaparin plasma clotting times are given aside for comparison as well as a saline control. Clotting times are the average of at least three replicate measurements using plasma from different blood donors with the error bars displaying the standard deviation. Concentrations of lPGS are given in mg/ml and concentrations of UFH and Tinzaparin are given in the corresponding amount of international units (IU/mg). Plasma with clotting times >500 seconds is indicated with a clotting time of 500 seconds, but without error bars. Results show that lPGS have similar activity as compared to heparins.

From FIG. 4 it becomes obvious that lPGS with a linear polyglycerol backbone of 3 kDa and high degree of sulfation (DS=100% equals 44 sulfate groups per molecule, lPG$_{3kDa}$S$_{44}$) and an overall molecular weight of 7.7 kDa has the same concentration dependent anti-coagulant profile in the aPTT assay as Tinzaparin with a molecular weight of 6.5 kDa. Similarly, lPG$_{5kDa}$S$_{60}$ with an overall molecular weight of 12.1 kDa exhibits a comparable aPTT profile as UFH, with a similar molecular weight on average but much broader polydispersity. As a general trend the anticoagulant properties of lPGS increase with increasing molecular weight of the backbone linear polyglycerol and constant high degree of sulfation. Thereby, the anticoagulant properties of lPGS remain evident as down to a concentration of 1.5 μg/ml. This is shown for three lPGS samples of various molecular weight of the backbone lPG in FIG. 5 via their respective concentration dependent aPTT times. Although at that low concentrations the anticoagulant properties as measured via aPTT are not strong, they are still detectable in vitro.

Figure 5:
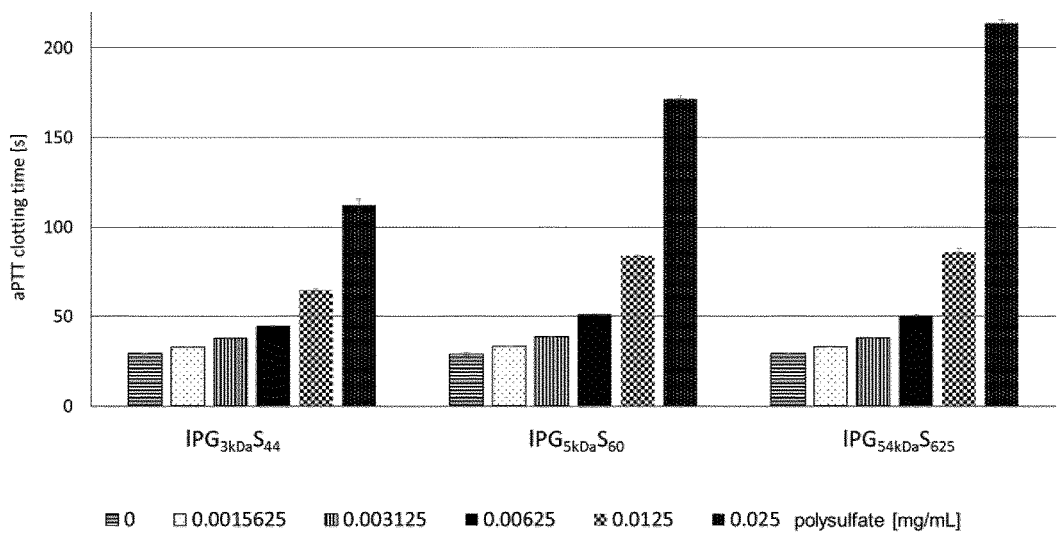
FIG. 5 shows aPTT plasma clotting times of selected lPGS samples at very low concentrations.

FIG. 5 shows aPTT plasma clotting times of selected lPGS samples at very low concentrations. Presented data are average values of at least triplicates with plasma from varying donors. Error bars illustrate standard deviations. Concentrations of 0 mg/ml correspond to the saline control. Data suggest the potent, concentration-dependent anticoagulation activity of lPGS molecules.

Figure 6:
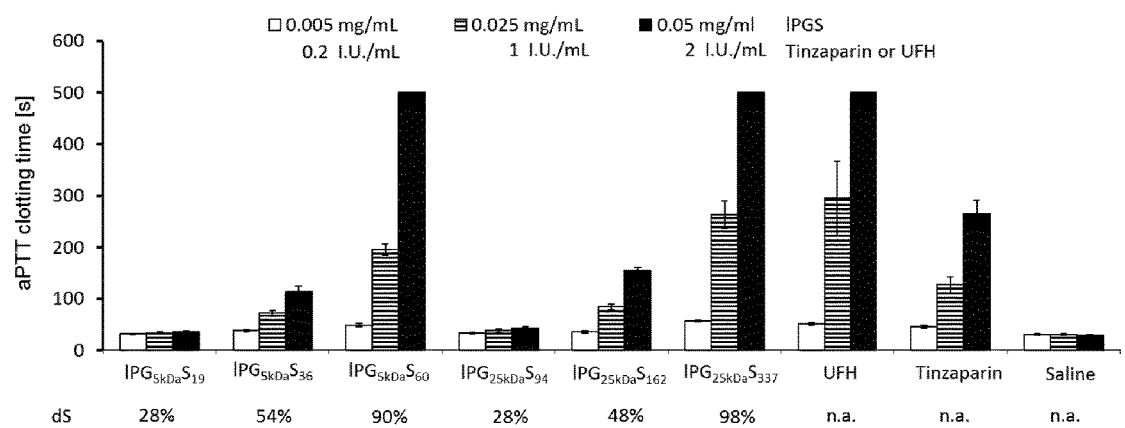
FIG. 6 shows concentration dependent aPTT clotting times of lPGS with constant molecular weight of the backbone (5 kDa and 25 kDa) but varying degree of sulfation (DS).

As illustrated in FIG. 6 the anticoagulant properties of lPGS with constant molecular weight of the backbone but varying number of sulfate groups per polymer, as exemplified with a series on a 5 and 25 kDa lPG backbone, increase with the DS. This clearly demonstrates the higher anticoagulant potential with augmented charge density on the polymer.

Specifically, FIG. 6 shows concentration dependent aPTT clotting times of lPGS with constant molecular weight of the backbone (5 kDa and 25 kDa) but varying degree of sulfation (DS) in comparison with UFH and Tinzaparin (n.a.=not applicable). Plasma with clotting times >500 seconds is indicated with a clotting time of 500 seconds, but without error bars.

Figure 7:
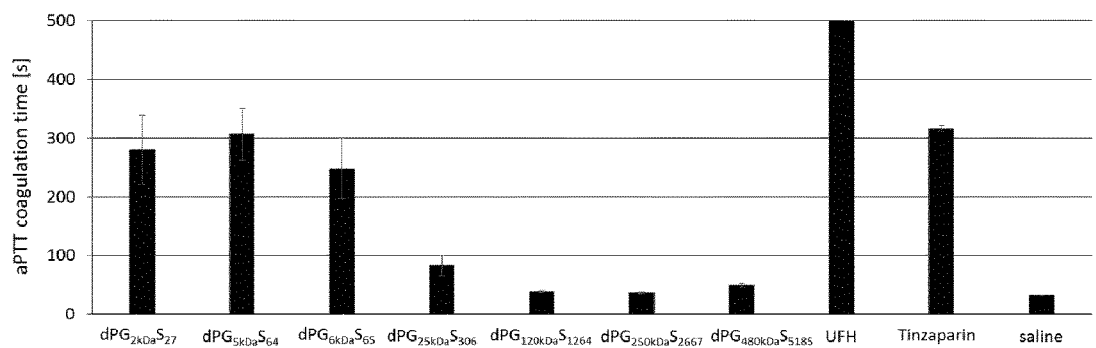
FIG. 7 shows aPTT plasma clotting times of dPGS samples with high degree of sulfation but varying molecular weight of the dendritic core.

In accordance with previous results, the anticoagulant properties of dendritic polyglycerol sulfate were found to be weaker than that of UFH for all molecular weights of dPGS evaluated in the aPTT plasma coagulation assay.[13] In FIG. 7 the aPTT times of different dendritic polyglycerol sulfates with a high degree of sulfation (78-100%), respectively, but varying molecular weight of the dendritic core are plotted for a fixed anticoagulant concentration of 0.05 mg/ml dPGS. Plasma with clotting times >500 seconds is indicated with a clotting time of 500 seconds, but without error bars. In contrast to lPGS, for which the anticoagulant effect increases or at least remains static with increasing molecular weight of the backbone (cf. FIG. 4), dPGS shows decreasing aPTT times with increasing molecular weight. At a molecular weight of the dendritic core of 120 kDa almost no anticoagulant properties (comparable to saline control) are found via aPTT for dPGS.

In order to better mimic the in vivo situation of coagulation whole blood is generally the better test medium than PPP since cellular components of blood, in particular platelets, play a crucial role in the process of clot formation. Thromboelastography (TEG) allows the tracking of blood clot formation and subsequent fibrinolysis of the formed clot from whole blood. In aPTT by default unnaturally fast contact activated blood coagulation times are measured (25-33 seconds for the untreated control) due to the use of aPTT reagents with unphysiological concentrations of phospholipids to mimic the membrane of platelets and ellagic acid activator for contact activation of the intrinsic pathway. [27]

Figure 8:
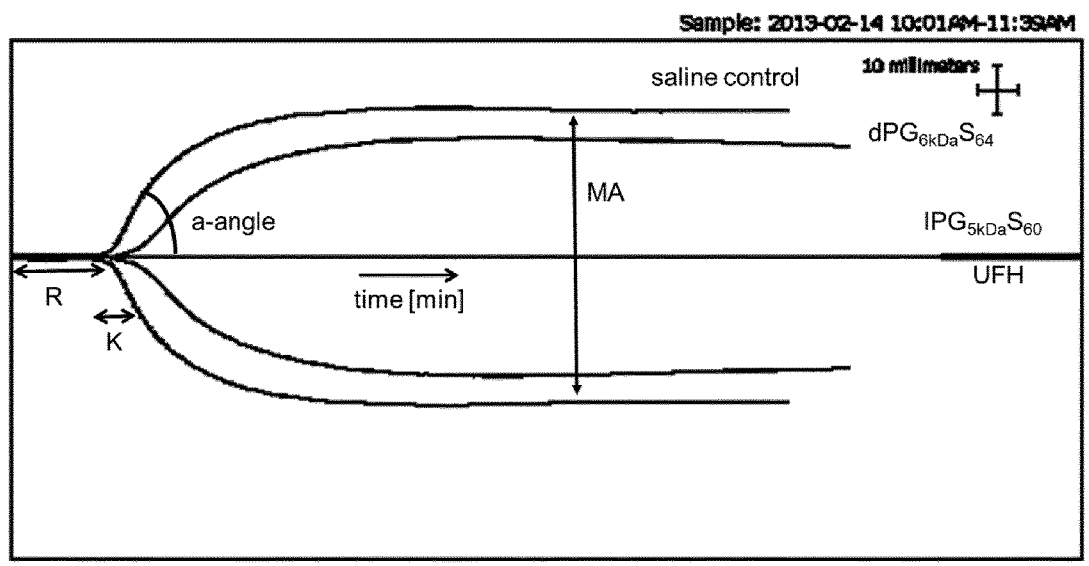
FIG. 8 shows representative thromboelastography (TEG) traces of $lPG_{5kDa}S_{60}$ and $dPG_{6kDa}S_{64}$ in fresh whole blood.

In contrast, thromboelastography is closer to the physiological conditions since only freshly donated, citrated whole blood is used which is recalcified by the addition of calcium chloride solution in order to initiate clotting. In FIG. 8 representative thromboelastography (TEG) traces of lPG$_{5kDa}$S$_{60}$ and dPG$_{6kDa}$S$_{64}$ in fresh whole blood in comparison with UFH and a saline control over the time course of one hour. The anticoagulant concentration was 0.05 mg/ml or 2 IU, respectively. Characteristic parameters like the R value (reaction time from the initiation of coagulation via recalcification to the first indication of clot formation), K value which is a measure for the speed of clot formation (the time from initial clot buildup until it reaches 20 mm), and the shape (□-angle and progression) of the curve as well as the maximum amplitude (MA) which is a measure of clot strength are indicated in FIG. 8. For the saline treated (considered as untreated) control blood a couple of minutes (strongly donor dependent, usually 7-13 minutes) after recalcification a symmetric deviation of the curve from the straight initial time line is observed which indicates the buildup of a blood clot. At some point of the curve the amplitude between the symmetrical curve is not growing any more but starts to decrease again (indicated with the MA arrow), which indicates endogenous fibrinolysis of the formed clot. UFH at a concentration of 2 IU/mg which roughly corresponds to 0.05 mg/ml polyglycerol sulfate showed no indication of clot formation during the time course of one hour in TEG since no typical curve shape development but only a straight line was observed. The same was true for $IPG_{5kDa}S_{60}$ at concentrations of 2 IU/mg which is why the two curves of UFH and lPGS in FIG. 8 overlap. When the TEG experiment was traced longer up to three hours UFH and $lPG_{5kDa}S_{60}$ at that concentration eventually showed initiated clotting with very slow rate of clot formation and very low amplitude, indicating very weak clot strength.

In strong contrast, $dPG_{6kDa}S_{64}$ at the same concentration revealed clear clot formation in whole blood and typical fibrinolysis after MA is reached (FIG. 8). Comparison of the later curve with the saline control shows that blood coagulation is slightly delayed by a couple of minutes (R value) as is the rate of clot formation (K value, □-angle). Clot strength (MA) with dPGS treated whole blood is a little weaker and the initiation of fibrinolysis is slightly delayed as compared to the saline control.

Hence, a TEG measurement is particularly well suited to reveal an authentic picture of the anticoagulant potential of lPGS and dPGS. Representative and characteristic parameters of TEG measurements with $IPG_{3kDa}S_{44}$, $IPG_{5kDa}S_{60}$, $dPG_{6kDa}S_{64}$ and UFH in whole blood are summarized in Table 2.

indication for concern (unpublished results). The fully synthetic nature of lPGS via a controlled polymerization mechanism make them superior to UFH and LMWHs. It eliminates the risk of disease transmission from animals to humans and yields structurally homogenous polymers with high degree of reproducibility and thus constant, adjustable, and reliable anticoagulant activity.

With respect to heparin induced thrombocytopenia (HIT) the molecular weight of lPGS or the chain length of the backbone, respectively, should be as short as possible to reduce the risk for HIT. HIT is a fatal immunogenic response which occurs very occasionally after heparin administration. It is induced by the binding of heparin to plasma circulation platelet factor 4 ($PF_4$) and a subsequent conformational change of $PF_4$ that leads to antibody recognition. For this conformational change to happen in $PF_4$, heparin must span the whole tetrameric protein equatorially which in turn requires a certain chain length of the polymer. By reducing the chain length of lPGS as far as possible but still keeping the anticoagulant properties, the risk for HIT development after lPGS administration can be reduced. Thus, out studies focused on lPGS samples with the shortest chain length but still good anticoagulant properties, i.e. $lPG_{3kDa}S_{44}$ and $lPG_{5kDa}S_{60}$.

TABLE 2

Representative and characteristic parameters of $IPG_{3\,kDa}S_{44}$, $IPG_{5\,kDa}S_{60}$, $dPG_{6\,kDa}S_{64}$ and UFH in TEG with whole blood.

| sample | concentration | R value [min] | K value [min] | MA [mm] | □-angle [°] |
| --- | --- | --- | --- | --- | --- |
| saline | — | 9.4 ± 2.7 | 2.7 ± 0.7 | 59 ± 4 | 54 ± 6 |
| $IPG_{3\,kDa}S_{44}$ | 0.05 mg/ml | 98 ± 48 | 27 ± 12 | 43 ± 3 | 20 ± 18 |
| $IPG_{5\,kDa}S_{60}$ | 0.05 mg/ml | 154 ± 27 | 32 ± 11 | 34 ± 4 | 5.7 ± 2.1 |
| $dPG_{6\,kDa}S_{64}$ | 0.05 mg/ml | 16 ± 3 | 2.8 ± 0.9 | 58 ± 8 | 53 ± 4 |
| UFH | 2 IU/ml | >120 | — | — | — |
| Tinzaparin | 2 IU/ml | >120 | — | — | — |

Stated values are the mean average ± standard deviation of at least two independent measurements with blood from different donors. For UFH no indication of coagulation is observed for up to 120 min, thus measurements were usually stopped after 120 minutes.

Form this table and the aPTT times given in FIGS. 4 and 7 it becomes obvious that even though $IPG_{3kDa}S_{60}$ and $dPG_{6kDa}S_{64}$ have similar clotting times between 200 and 300 seconds in the aPTT assay at a concentration of 0.05 mg/ml, clotting times and curve profiles from TEG measurements of the two samples in whole blood at the same concentration are vastly different. This clearly demonstrates the importance of TEG measurements in whole blood in order to verify the obtained results from conventional in vitro plasma coagulation assays that require additional activating agents.

The majority of polysulfated or polyanionic polymers with known anticoagulant properties in vitro, like commercial polyvinyl sulfate sodium (PVS), polystyrene sulfonate sodium (PSS) and others were often identified only by conventional aPTT coagulation assays with PPP and are not very promising for in vivo application due to unknown toxicity profiles or biocompatibility issues.

Figure 9:
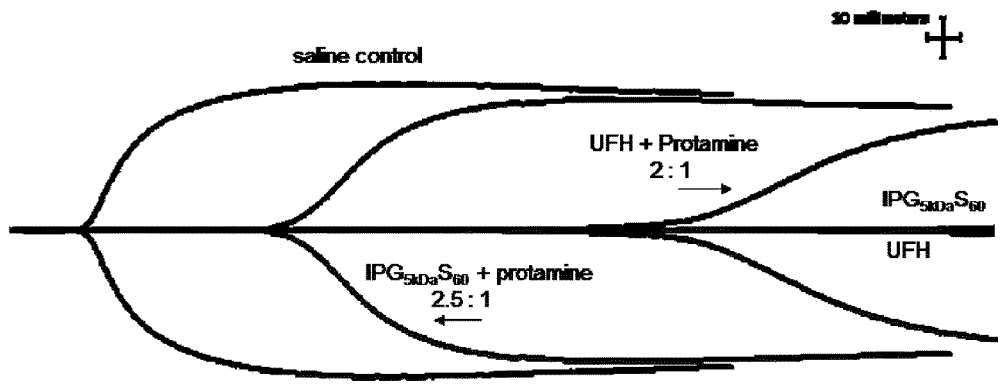
FIG. 9 shows representative TEG curves of whole blood with UFH (2 IU/ml) and $lPG_{5kDa}S_{60}$ (0.05 mg/ml) in the presence and absence of protamine.

Hence, lPGS as a surprisingly effective anticoagulant (similarly effective as Tinzaparin or UFH) in whole blood. It is based on a highly biocompatible linear polyglycerol backbone, thus the chance for biocompatibility issues are low. In fact, all studies concerning hemo- or biocompatibility of lPGS such as red blood cell aggregation, in vitro cell toxicity or a functional platelet assay did not show any A requirement for a safe drug is the existence of a fast and effective antidote that quenches the effect of the drug in case of accidental overdosing or adverse, unwanted response of the patient to the drug. Protamine sulfate is an FDA approved, effective antidote for UFH and can also reverse the action of lPGS. This can be seen from FIG. 9 showing representative TEG curves of whole blood with UFH (2 IU/ml) and $IPG_{5kDa}S_{60}$ (0.05 mg/ml) in the presence and absence of protamine. The plot shows recorded curves up to 150 minutes. Addition of protamine to UFH or lPGS treated whole blood reverses the respective anticoagulant (flat, straight TEG curves) effect and induces regular clot formation similar to the saline control. Below the curve characteristic parameters of these TEG experiments are listed.

The strongly anticoagulated whole blood (UFH and $IPG_{5kDa}S_{60}$) as indicated by the overlapping flat, straight lines in the TEG trace was brought back into a clotting state after mixing with protamine in a 2:1 or 2.5:1 ratio, respectively. The corresponding TEG traces of the protamine treated anticoagulated whole blood samples show a similar shape as the saline control and hence indicate successful reversal of the anticoagulant effect for both UFH and lPGS. Characteristic parameters of these TEG curves are given in the table 3 below.

TABLE 3

Characteristic parameters of the TEG curves of FIG. 9.

| sample | anticoagulant concentration | R value [min] | K value [min] | MA [mm] | □-angle |
|---|---|---|---|---|---|
| saline | — | 11.3 | 3.3 | 55.6 | 48.9 |
| $IPG_{5\,kDa}S_{60}$ | 0.05 mg/ml | 140.2 | 36.9 | n.a. | n.a. |
| $IPG_{5\,kDa}S_{60}$: protamine (2.5:1) | 0.05 mg/ml | 37.9 | 8.2 | 49.7 | 27.4 |
| UFH | 1 IU/ml | 191.1 | n.a. | n.a. | n.a. |
| UFH:protamine (2:1) | 1 IU/ml | 87.7 | 18.8 | 42.9 | 9.5 | n.a. = not applicable since the curve shape does not allow the measurement

The neutralizing effect of protamine on lPGS can also be verified via aPTT measurements in plasma as shown in Table 4. Similarly to UFH the effective amount of protamine to quench the charges of the polysulfate and thus neutralize the anticoagulant effect strongly depends on the respective donor blood and needs to be determined via titration experiments as demonstrated in Table 4. Protamine when overdosed (overtitrated) has a strong anticoagulant effect itself which is one of the major disadvantageous of protamine as an antidote for heparins in clinical settings.

TABLE 4

Summary of clotting times of $IPG_{5\,kDa}S_{60}$ treated plasma in the presence and absence of protamine via aPTT.

| sample | anticoagulant concentration | AC/P ratio * | clotting time [s] |
|---|---|---|---|
| saline | — | — | 31.2 ± 0.6 |
| $IPG_{5\,kDa}S_{60}$ | 0.05 | — | >500 |
| $IPG_{5\,kDa}S_{60}$:protamine | 0.05 | 2:1 | 250 ± 10 |
| $IPG_{5\,kDa}S_{60}$:protamine | 0.05 | 1:1 | 111 ± 4 |
| $IPG_{5\,kDa}S_{60}$:protamine | 0.05 | 1:2 | 45.6 ± 1.1 |
| $IPG_{5\,kDa}S_{60}$:protamine | 0.05 | 1:4 | >500 |

Stated values are average ± standard deviation from two independent experiments with plasma from different donors.
* anticoagulant/protamine ratio Table 5 summarizes the neutralizing effect of the universal heparin binding polymer (UHBP) as described in reference [22] on lPGS with and demonstrates its efficiency as antidote for lPGS.

TABLE 5

Summary of clotting times of $IPG_{3\,kDa}S_{44}$ and $IPG_{5\,kDa}S_{60}$ treated plasma in the presence and absence of UHBP-1 as a neutralizing agent measured via aPTT.

| Sample | anticoagulant concentration [mg/ml] | AC/U ratio* | clotting time [s] |
|---|---|---|---|
| saline | — | — | 29.7 ± 1.3 |
| $IPG_{3\,kDa}S_{44}$ | 0.05 | — | 339 ± 57 |
| $IPG_{3\,kDa}S_{44}$:UHBP-1 | 0.05 | 2:1 | 104 ± 26 |
| $IPG_{3\,kDa}S_{44}$:UHBP-1 | 0.05 | 1:1 | 62 ± 2 |
| $IPG_{3\,kDa}S_{44}$:UHBP-1 | 0.05 | 1:2 | 30.2 ± 1.3 |
| saline | — | — | 30.3 ± 1.4 |
| $IPG_{5\,kDa}S_{60}$ | 0.05 | — | >500 |
| $IPG_{5\,kDa}S_{60}$:UHBP-1 | 0.05 | 2:1 | 244 ± 85 |
| $IPG_{5\,kDa}S_{60}$:UHBP-1 | 0.05 | 1:1 | 67 ± 12 |
| $IPG_{5\,kDa}S_{60}$:UHBP-1 | 0.05 | 1:2 | 30.0 ± 1.2 |

Stated values are average ± standard deviation from at least three independent experiments (in double determination) with PPP from different donors.
*anticoagulant/UHBP ratio The used UHBP-1 is based on a 23 kDa dendritic polyglycerol statistically modified by 8 heparin binding groups. These groups consist of tertiary amine clusters which are protonated under physiological pH and hence yield a polymer with 8 positively charged amino clusters. The overall amount of positively charged tertiary amine groups per polymer at physiological pH was 24 for the UHBP which was used in the study summarized in Table 5. The design of this UHBP is as such that an mPEG (450 Da) shell on the surface of the dendritic polyglycerol was installed in order to improve biocompatibility of the positively charged polymer.

A similar neutralizing effect for the anticoagulant properties of $IPG_{3kDa}S_{44}$ on PPP was observed with a UHBP which had a lower molecular weight of the dendritic core (10 kDa) and lower amount of tertiary amine groups per molecule (7 and 5, respectively). The one corresponding to 7 amine groups denoted as UHBP-2 and the one with 5 amine groups per molecule denoted as UHBP-3. Here, UHBP-2 proofs to be slightly more efficient in its neutralizing efficiency for $IPG_{3kDa}S_{44}$ than UHBP-3. When comparing clotting times of the respective ratios of lPGS to UHBP (Table 5) for UHBP-2 and UHBP-3, the former one consistently yields clotting times closer to the one of the saline control. Although this trend is minimal, it is in line with the composition of the respective UBHP, since UBHP-2 bears more amine groups per polymer than UHBP-3 and hence has higher capacity to quench the anionic charges of lPGS. In accordance with its structural feature of presenting the highest amount of positive charges per molecule among the three UHBPs (Table 5 and 6), UHBP-1 is identified as the most effective neutralizing agent for lPGS in the aPTT assay.

TABLE 6

Summary of aPTT clotting times of $IPG_{3\,kDa}S_{44}$ treated plasma in the presence and absence of UHBP-2 and UHBP-3 as a neutralizing agent at different ratios.

| Sample | anticoagulant concentration [mg/ml] | AC/U ratio* | clotting time [s] |
|---|---|---|---|
| saline | — | — | 30.7 ± 1.7 |
| $IPG_{3\,kDa}S_{44}$ | 0.05 | — | 362 ± 70 |
| $IPG_{3\,kDa}S_{44}$:UHBP-2 | 0.05 | 2:1 | 122 ± 14 |
| $IPG_{3\,kDa}S_{44}$:UHBP-2 | 0.05 | 1:1 | 62 ± 10 |
| $IPG_{3\,kDa}S_{44}$:UHBP-2 | 0.05 | 1:2 | 34.8 ± 2.2 |
| saline | — | — | 31.0 ± 1.4 |
| $IPG_{3\,kDa}S_{44}$ | 0.05 | — | 369 ± 77 |
| $IPG_{3\,kDa}S_{44}$:UHBP-3 | 0.05 | 2:1 | 156 ± 21 |
| $IPG_{3\,kDa}S_{44}$:UHBP-3 | 0.05 | 1:1 | 97 ± 9 |
| $IPG_{3\,kDa}S_{44}$:UHBP-3 | 0.05 | 1:2 | 43.3 ± 3.0 |

Stated values are average ± standard deviation from at least five independent experiments (in double determination) with PPP from different donors.
*anticoagulant/UHBP ratio In order to verify the aPTT based results concerning the antidote efficiency and to make sure that UHBP-1 will also neutralize the anticoagulant effect of lPGS in whole blood TEG measurements were performed with $IPG_{5kDa}S_{60}$ treated whole blood and UHBP-1 at different ratios. A summary of the characteristic TEG curve parameters in the presence and absence of UHBP-1 is given in Table 7. First of all the TEG measurements confirm the efficiency and safety of UHBP-1 as an antidote to lPGS also in whole blood. Comparison with analogous data in PPP via aPTT reveal a ratio of lPGS: UHBP-1 of 1:1 as sufficient for complete reversal of the anticoagulant properties of $IPG_{5kDa}S_{60}$ in whole blood, while data obtained from aPTT measurements with PPP would suggest a ratio 1:2 for exhaustive reversal. In addition, this TEG data confirms the previous finding that UHBP is superior to protamine sulfate since overdosing (or overtitrating as for lPGS:UHBP-1 of 1:1.5 and 1:2) did not lead to any anticoagulant effect on whole blood and thus could be the safer antidote in clinical settings.[28]

TABLE 7

Summary of characteristic and representative TEG curve parameters for IPG$_{5\,kDa}$S$_{60}$ (0.05 mg/ml) treated whole blood in the presence and absence of UHBP-1 with various anticoagulant to antidote ratios.

| Sample | AC/U ratio* | R value [min] | K value [min] | MA [mm] | ∎-angle [°] |
|---|---|---|---|---|---|
| saline | — | 9.4 ± 2.7 | 2.7 ± 0.7 | 59 ± 4 | 54 ± 6 |
| IPG$_{5\,kDa}$S$_{60}$ | — | 154 ± 27 | 32 ± 11 | 34 ± 4 | 5.7 ± 2.1 |
| IPG$_{5\,kDa}$S$_{60}$:UHBP-1 | 2:1 | 41 ± 8 | 14.5 ± 4.8 | 41 ± 3 | 15 ± 2 |
| IPG$_{5\,kDa}$S$_{60}$:UHBP-1 | 1:1 | 9.0 ± 1.7 | 2.8 ± 0.9 | 56 ± 3 | 52 ± 6 |
| IPG$_{5\,kDa}$S$_{60}$:UHBP-1 | 1:1.5 | 8.4 ± 0.6 | 2.6 ± 0.4 | 61 ± 3 | 57 ± 3 |
| IPG$_{5\,kDa}$S$_{60}$:UHBP-1 | 1:2 | 7.6 ± 0.4 | 2.2 ± 0 | 60 ± 0 | 60 ± 1 |

Stated values are average ± standard deviation from at least two independent experiments with whole blood from different donors.
*anticoagulant/UHBP ratio Blood coagulation is generally described by the cascade like waterfall diagram of coagulation enzymes and zymogens which is divided into the intrinsic or contact activation pathway, the extrinsic or tissue factor pathway and the common pathway.[29-31] Heparins or their anticoagulant efficiency, respectively in blood or plasma is usually tested via the aPTT assay in PPP (see FIG. 3). This assay tests for the intrinsic and common pathway of coagulation. Via the prothrombin time (PT assay) the extrinsic pathway can be analyzed. However, when working with polyanionic anticoagulants it is important to use a thromboplastin reagent for this assay that is sensitive for heparins. Since the latter two in vitro assays are standard in clinics where heparinized blood is commonly analyzed via the aPTT assay, many PT reagents contain additional protamine sulfate. This will neutralize any heparin present in the sample and allow the study of the extrinsic pathway independent of heparin. Thromboplastin reagents contain phospholipids and tissue factor as the active components which initiate the extrinsic pathway of coagulation. Since heparins only interfere with FXa within this pathway only moderate effects of heparins on PT coagulation times are observed, provided that the thromboplastin reagent is sensitive towards heparins, otherwise no effect at all will be detected from heparins. The conventional PT assay activates coagulation with a very high concentration of tissue factor and phospholipids in the thromboplastin PT reagent which is far of any physiological relevance. Hence, typical clotting times in the PT assay are fast compared to clotting times in the aPTT assay. Normal, human PPP from healthy donors usually has clotting times around 10 seconds. In order to mimic more physiological conditions variants of this PT assay have been developed that use diluted thromboplastin agent in order to end up at more physiological concentrations of phospholipids and tissue factor which consequently enhances the observed coagulation times.[32] Such a variation of the PT assay (e.g. 100 times dilution of the thromboplastin agent added) is generally termed dilute PT assay and aims at coagulation times of 30-60 seconds with normal human PPP.

Figure 10:
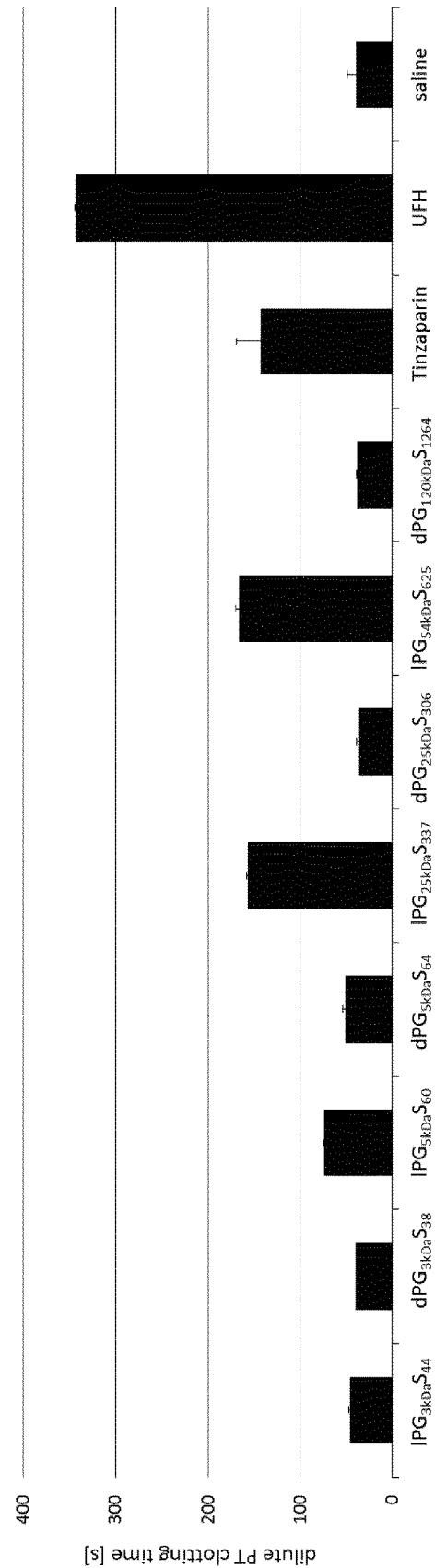
FIG. 10 shows dilute prothrombin (PT) plasma clotting time of lPGS, dPGS, tinzaparin and UFH at a concentration of 0.05 mg/ml and 2 IU/ml, respectively.

A compilation of the dilute PT clotting times of lPGS, dPGS, tinazaparin and UFH treated human PPP at a concentration of 0.05 mg/ml and 2 IU/ml, respectively, generated with a heparin sensitive thromboplastin reagent is given in FIG. 10. Stated values are average±standard deviation from at least three independent experiments using whole blood from different donors. LPGS shows a moderate increase in clotting time with increasing molecular weight of the lPG backbone and a constant high degree of sulfation, respectively. Just at high molecular weight of the lPG backbone of 25 kDa and higher a similar effect on blood coagulation as the one from LMWH tinzaparin is observed in the dilute PT assay. In contrast, independent of molecular weight almost no influence on PT clotting time is observed for dPGS treated PPP when compared to the saline control. In strong contrast, UFH with an average molecular weight of 12 kDa exhibits a strong anticoagulant effect in the extrinsic pathway of blood coagulation compared to polyglycerol sulfates. This can be interpreted as a first indication for a different and completely unexpected anticoagulant mechanism or mode of action of lPGS compared to heparins.

Figure 11:
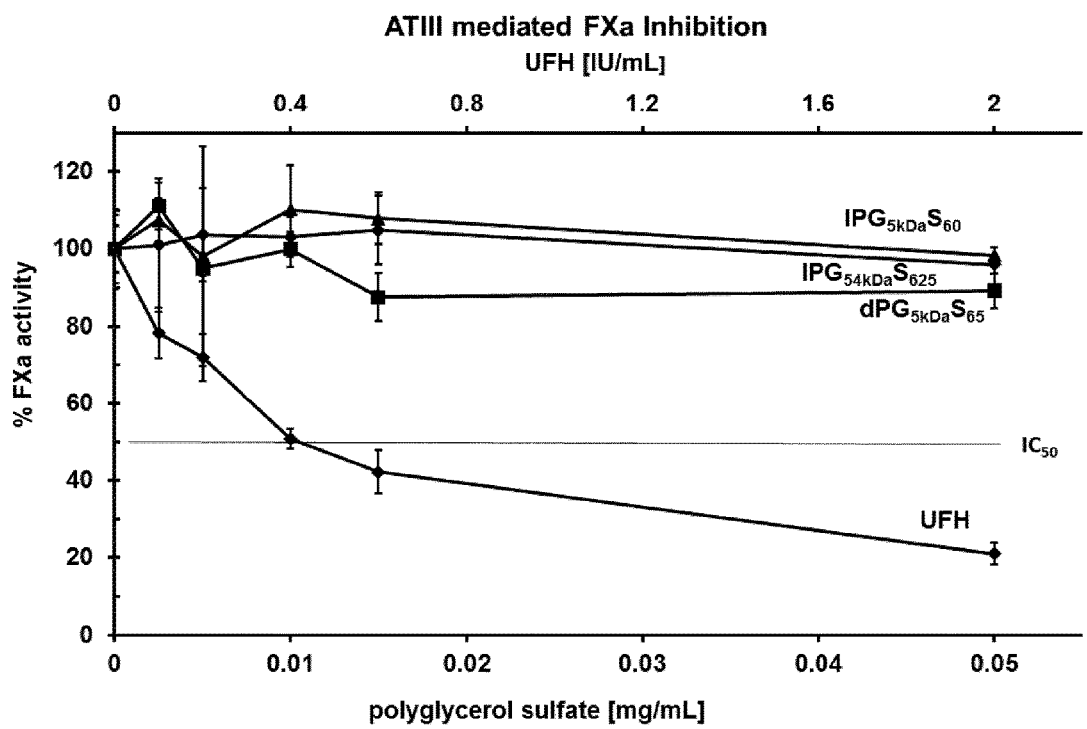
FIG. 11 shows concentration dependent inhibition of FXa by UFH, lPGS and dPGS in the presence of ATIII via activity measurement of FXa in a chromogenic FXa assay.

For elucidation of the mode of action of lPGS chromogenic assays with purified enzymes in buffer and a suitable chromogenic substrate for the respective enzyme are used in the presence and absence of the anticoagulant. Thereby, the rate of dye development from enzymatic cleavage of the chromogenic substrate is measured on a UV plate reader at the respective wavelength at fixed concentration of the enzyme, excess substrate and various concentrations of the inhibitor of the enzyme, i.e. the anticoagulant. Since heparins (UFH and LMWH) mainly inhibit FXa and Thrombin (FIIa) in an indirect fashion via activation of circulating, endogenous ATIII during blood coagulation, purified ATIII has to be added in sufficient amounts to the chromogenic assay mixture when heparins efficiency as an inhibitor to FXa and FIIa is assayed. FIG. 11 shows the respective concentration dependent inhibition of FXa with lPGS, dPGS and UFH at a fixed ATIII concentration. lPGS of low and high molecular weight at a high degree of sulfation (IPG$_{5kDa}$S$_{60}$ and IPG54$_{kDa}$S$_{625}$), respectively, as well as dPG$_{5kDa}$S$_{65}$ reveal no effect at all on FXa. In strong contrast, UFH shows a concentration dependent inhibition of FXa as expected. This finding explains the observed differences in PT clotting time between polyglycerol sulfates and UFH, since the former does not inhibit FXa which is the main factor in the extrinsic pathway of blood coagulation.

FIG. 11 shows the concentration dependent inhibition of FXa by UFH, lPGS and dPGS in the presence of ATIII via activity measurement of FXa in a chromogenic FXa assay. The y-axis on top refers to the UFH concentration in IU/ml the one on the bottom to the corresponding polyglycerol sulfate concentration in mg/ml. Data are average of three replicates±standard deviation.

A similar assay with thrombin instead of FXa and a different chromogenic substrate with high specificity for thrombin revealed that thrombin is inhibited by lPGS and dPGS to a similar degree as by UFH in a purified buffer system with ATIII added. Compared with TEG and aPTT data in whole blood and PPP this finding suggests that dPGS is not as available as lPGS in plasma which is why in plasma lPGS is a much better anticoagulant than dPGS even though affinity for thrombin in the purified system is comparable and in the same range as heparins ATIII mediated affinity for thrombin.

Figure 12:
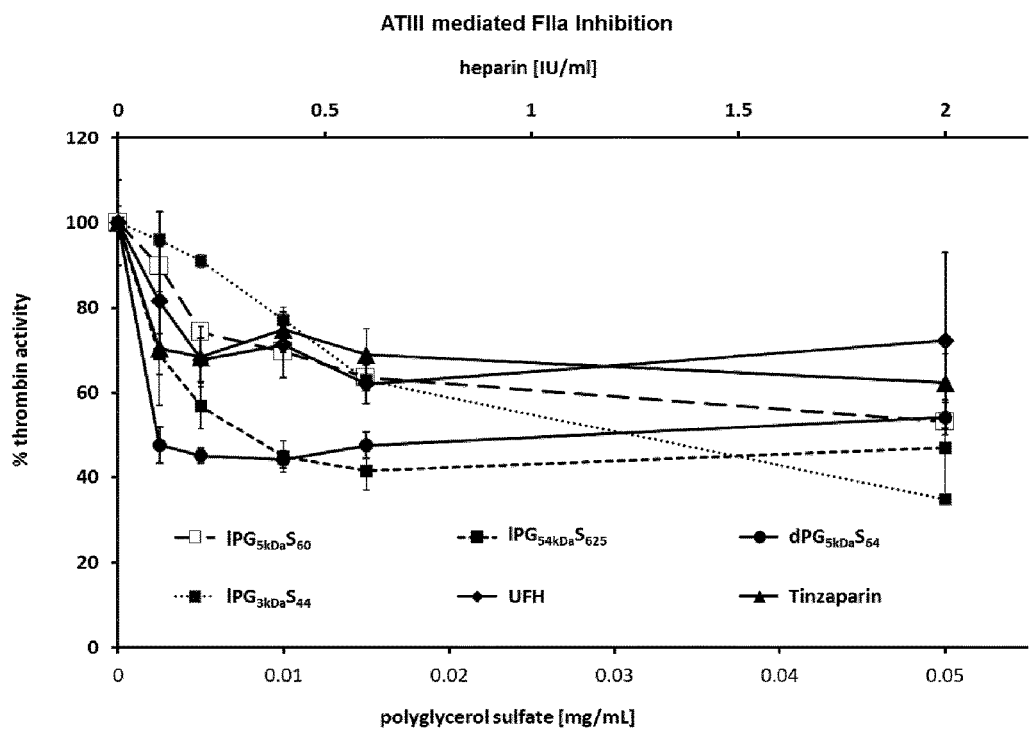
FIG. 12 shows concentration dependent inhibition of FIIa by UFH, lPGS and dPGS in the presence of ATIII via thrombin activity measurement in a chromogenic FIIa assay.

The result are depicted in FIG. 12 that shows concentration dependent inhibition of FIIa by UFH, lPGS and dPGS in the presence of ATIII via thrombin activity measurement in a chromogenic FIIa assay. The y-axis on top refers to the UFH concentration in IU/ml the one on the bottom to the corresponding polyglycerol sulfate concentration in mg/ml. Data are average of three replicates±standard deviation.

Figure 13:
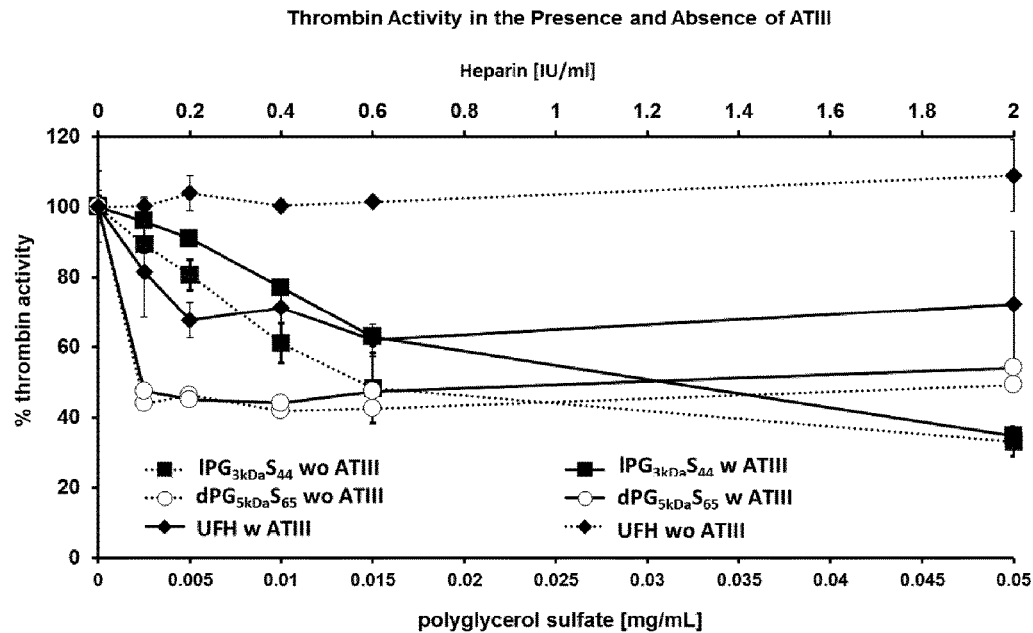
FIG. 13 shows concentration dependent inhibition of FIIa by UFH, lPGS and dPGS in the absence of ATIII via thrombin activity measurement in a chromogenic FIIa assay.

An alternative scientific explanation for the differences in anticoagulation of lPGS and dPGS could be an additional target within the coagulation cascade that is only addressed by the linear but not the dendritic polyglycerol sulfate and hence results in the vastly different anticoagulant efficiency of the latter two in vitro. The thrombin activity in the presence of UFH, lPGS and dPGS in an identical chromogenic assay as described above but without addition of ATII to the purified system yields the expected result for UFH as illustrated in FIG. 13. Specifically, FIG. 13 shows concentration dependent inhibition of FIIa by UFH, lPGS and dPGS in the absence of ATIII via thrombin activity measurement in a chromogenic FIIa assay. The y-axis on top refers to the UFH concentration in IU/ml the one on the bottom to the corresponding polyglycerol sulfate concentration in mg/ml. Data are average of three replicates±standard deviation.

Since heparins require ATIII in order to inhibit FXa and FIIa no effect on thrombin activity is observed for UFH in the absence of ATIII. Surprisingly, identical thrombin inhibition is observed for lPGS and dPGS in the presence and absence of ATIII which indicates that the anticoagulant effect of polyglycerol sulfates is due to a direct inhibition of thrombin rather than an indirect ATIII mediated heparin analog inhibition mechanism.

This mechanistic hypothesis for lPGS and dPGS is supported by the measured $K_d$ values for thrombin and ATIII via microscale thermophoresis (MST) measurements, a label free technique for the determination of dissociation constants in solution. The experiments were performed with a Monolith NT.LabelFree instrument (NanoTemper, Munich, Germany) which allows to determine dissociation constants in solution. Since this device can only detect $K_d$ values in the medium affinity range but not very high and very low $K_d$ values in the high mM range were assigned as not binding (n.b.) in Table 7. As expected non-sulfated linear and dendritic polyglycerol does not exhibit any affinity for the blood coagulation enzymes ATIII or thrombin, which is in line with their perfect haemocompatibilty as published earlier. [16-17] Also in agreement with the data shown in FIG. 11 lPGS and dPGS does bind to FIIa, while lPGS (high nM range) shows a much higher affinity for Thrombin than dPGS (high nM vs. low μM range). In contrast, heparin shows a significantly higher affinity to ATIII.

TABLE 8

$K_d$ values of $IPG_{5\,kDa}S_{60}$, $dPG_{5\,kDa}S_{65}$ and UFH (14 kDa) as well as for the non-sulfates controls $IPG_{5\,kDa}$ and $dPG_{5\,kDa}$ for purified human thrombin and ATIII at 25° C. in Dulbeccos phosphate buffered saline, pH 7.4.

| Kd | UFH | $IPG_{5\,kDa}S_{60}$ | $IPG_{5\,kDa}$ | $dPG_{5\,kDa}S_{60}$ | $dPG_{5\,kDa}$ |
|---|---|---|---|---|---|
| ATIII [μM] | 0.25 ± 0.15 | n.b. | n.b. | n.b. | n.b. |
| FIIa [μM] | 23 ± 5 | 0.9 ± 0.5 | n.b. | 9 ± 8 | n.b. | n.b. = no binding or > mM

Figure 14:
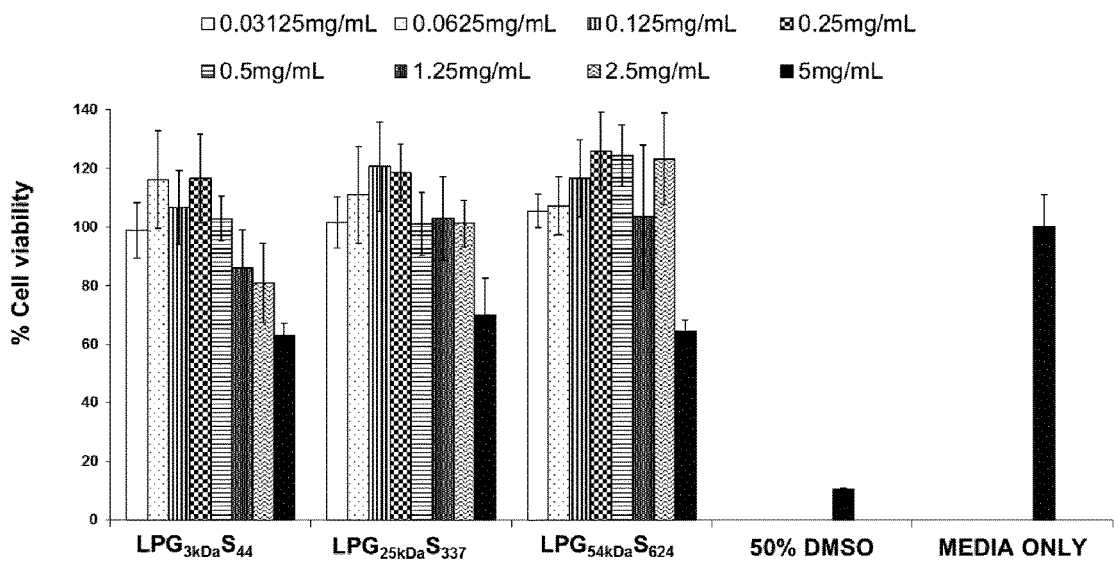
FIG. 14 shows in vitro cell toxicity of HUVECs after 24 h exposure to lPGS with different molecular weights.

In order to evaluate the cellular compatibility of lPGS dependent on the molecular weight (FIG. 14) and the degree of sulfation (FIG. 15), an MTS cytotoxicity assay with human umbilical vein endothelial cells (HUVECs) was conducted. This calorimetric assay is based on the enzymatic conversion of a dye and quantitatively describes the number of viable cells present. As can be seen in FIG. 14, up to a concentration of 2.5 mg/mL the cell viability is, independent of the molecular weight, not affected (≥80%). At a concentration of 5 mg/mL a reduction of the viability to 60% was found, however, the highest concentrations applied in this assay are not relevant for the application of lPGS. Specifically, FIG. 14 shows normalized values on in vitro cell toxicity of HUVECs after 24 h exposure to lPGS with different molecular weights. 100%: media only. Negative control: DMSO. Furthermore, the cell viability is independent (≥80%) of the degree of sulfation (5 kDa scaffold) up to a concentration of 2.5 mg/mL (FIG. 15) which confirms the good cell compatibility of lPGS.

Figure 15:
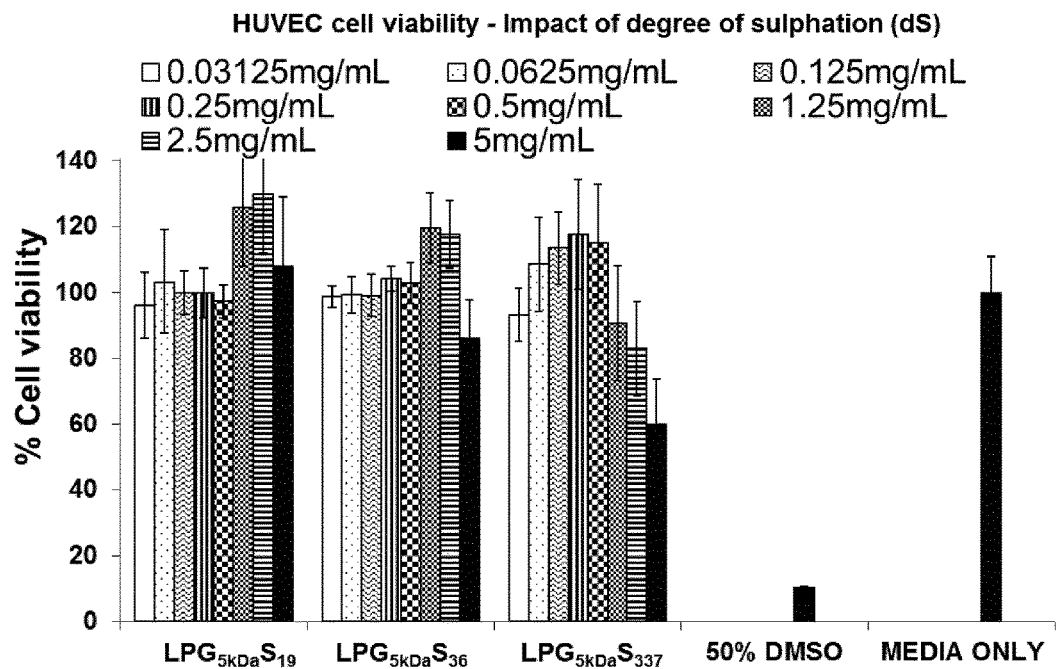
FIG. 15 shows in vitro cell toxicity of HUVEC's after 24 h exposure of lPGS (backbone=5 kDa) with different degree of sulfation.

FIG. 15 shows normalized values on the in vitro cell toxicity of HUVEC's after 24 h exposure of lPGS (backbone=5 kDa) with different degree of sulfation.100%: media only. Negative control: DMSO.

The in vivo efficacy of lPGS was proven for $IPG_{3kDa}S_{44}$ and $IPG_{5kDa}S_{60}$ by the determination of the aPTT clotting time of platelet poor plasma (PPP) samples obtained from rats after i.v. bolus injection of 0.0625 mg/mL at indicated time points (Tables 9 and 10). The given data are from PPP of freshly drawn blood which were measured at the same day. As can be seen from Table 8, a prolongation of the aPTT in the first hour after i.v. administration was observed when treated with $IPG_{3kDa}S_{44}$. Reduction of the aPTT to control levels (−15 min.) was observed 4 hours after the injection. In contrast, $IPG_{5kDa}S_{60}$ had a more pronounced anticoagulant effect for longer than one hour (Table 10). These profiles clearly show that a reproducible anticoagulant effect is obtained in vivo and that the temporal evolution can be influenced by the molecular weight of the lPGS.

TABLE 9 aPTT of platelet poor plasma at given time points after i.v. injection of $IPG_{3\,kDa}S_{44}$.

| Time [min] | aPTT [s] Animal 1 | aPTT [s] Animal 2 | aPTT [s] Animal 3 | aPTT [s] Animal 4 |
|---|---|---|---|---|
| −15 | 21.2 | 28.4 | 26.9 | 25.4 |
| 5 | >500 | 206.7 | 104.7 | 228.5 |
| 10 | 202.3 | 146.0 | 162.0 | 175.7 |
| 30 | 91.5 | 52.5 | 71.3 | 54.2 |

TABLE 9-continued aPTT of platelet poor plasma at given time
points after i.v. injection of $IPG_{3\,kDa}S_{44}$.

| Time [min] | aPTT [s] Animal 1 | aPTT [s] Animal 2 | aPTT [s] Animal 3 | aPTT [s] Animal 4 |
|---|---|---|---|---|
| 60 | 30.0 | 32.2 | 46.2 | — |
| 240 | 18.3 | 20.5 | 18.7 | 19.3 |

−15 minutes refers to control plasma drawn 15 minutes prior to bolus injection.
n.a. = data not available (clotting of blood during blood draw or clotting before reconstitution even without Ca addition).

TABLE 10 aPTT of platelet poor plasma at given time
points after i.v. injection of $IPG_{5\,kDa}S_{60}$.

| Time [min] | aPTT [s] Animal 1 | aPTT [s] Animal 2 | aPTT [s] Animal 3 | aPTT [s] Animal 4 |
|---|---|---|---|---|
| −15 | 19.6 | 15.0 | 26.9 | 25.4 |
| 5 | >500 | >500 | >500 | >500 |
| 10 | >500 | >500 | >500 | 397.6 |
| 30 | 496.4 | 406.5 | >500 | 192.1 |
| 60 | 116.0 | 113.5 | 163.1 | 110.1 |
| 240 | 14.8 | 14.5 | — | — |

−15 minutes refers to control plasma drawn 15 minutes prior to bolus injection.
n.a. = data not available (clotting of blood during blood draw or clotting before reconstitution even without Ca addition).

Surface Immobilization of lPGS

Preventing the activation of the coagulation pathway and hence thrombus formation is a major issue in many medical applications where devices come in contact with blood. However, coating of a material with a protective layer that can be optimized with respect to its anticoagulant properties still remains an unsolved problem. In addition, the device to be functionalized can be made up of a variety of materials which requires a universal approach to efficiently coat the device. Compared to non-covalent approaches where an anticoagulant layer, for example heparin, is physically adsorbed to the surface, covalent immobilization prevents it from being removed, thereby entering the bloodstream, and possibly exhibiting uncontrolled biological activity. In case of covalently immobilized heparin it is believed that the undefined linkage to the surface influences the anticoagulant activity to a major part. Since heparin is poorly homogeneous and has multiple reactive groups at different sites of the polymer only a statistical functionalization of surface immobilizing moieties (anchors) can be realized and by this the anticoagulant properties can hardly be adjusted.

Figure 16A:
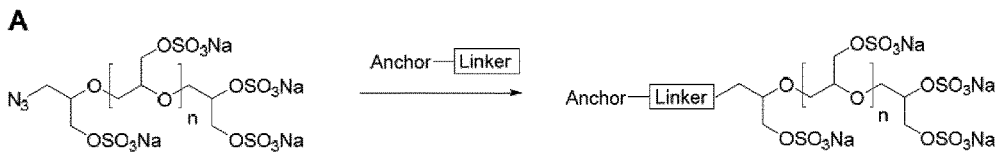
FIG. 16 shows representative synthetic schemes of lPGS with an anchor group for surface immobilization.

In contrast, lPGS bearing one single functional group, such as an azide function, located at the terminus of the polymer chain, can be used to conjugate one single anchor to the end of the polymer. This is shown in FIG. 16 depicting representative synthesis schemes of lPGS with an anchor group for surface immobilization. The terminal azide of the lPGS allows mono functionalization of the polymer scaffold (FIG. 16A). Conjugation is realized by azide-alkyne "click" chemistry with either Cu(I) as catalyst (R═H) or catalyst-free by strain promoted cyclooctyne-alkyne click conjugation. The gold surface is representative only.

Figure 16B:
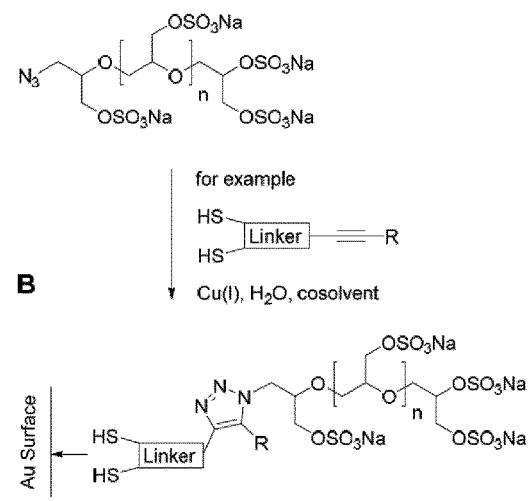

By this, control over the localization of the anchor, constitution and length of the linker, as well as the type of anchor which determines the surface to be functionalized, is guaranteed. FIG. 16B representatively illustrates how a gold surface is covalently functionalized with lPGS by using a dithol as the anchor group. This modular approach allows the design of the linker and lPGS separately and offers remarkable advantages compared currently applied covalent and non-covalent approaches. The material to be functionalized can be either a macroscopic material like a medical device or a particle and the surface can be made of any material. The most common materials are glass, plastic, or metal.

The above described immobilization of lPGS was established on gold nanoparticles in order to confirm the anticoagulant properties of a modified surface via TEG.

In summary, lPGS is a fully synthetic, structurally homogenous polymer with high anticoagulant properties. Due to the fully synthetic nature, and the anionic polymerization method molecular weights can easily be adjusted to the desired range from a couple of 150 Da to several 100,000 kDa with control over the end group and low polydispersity. End-group control with reactive entities at the terminal side of the linear polymer chain allows covalent modification of surfaces with lPGS for the fabrication of anti-thrombotic surfaces. In addition the fully synthetic nature of lPGS eliminates the risk of disease transmission from animals. The structural homogeneity of lPGS guarantees predictability and adjustability of the anticoagulant properties via the molecular weight (chain length of the lPG precursor) and the degree of sulfation. Moreover, in contrast to fondaparinux or LMWHs a 100% effective and FDA approved antidote for lPGS is available. The short chain length at which lPGS shows already high anticoagulant properties in whole blood are promising to eliminate adverse immune response from $PF_4$ binding.

Applications of lPGS are in the clinical, therapeutic and diagnostic area as new fully synthetic and thus safer, structurally homogeneous anticoagulants for in vitro and in vivo use. Opportunities are emerging as a new drug but also as a tool for in vitro blood diagnostics. In addition, the convenient chance for end group functionalization of these polymers offer possibilities for chemical, covalent surface modification with these polysulfates for the generation of anti-thrombotic surfaces on implants and devices such as for blood storage bags, catheters, blood pumps (artificial hearts), blood collection vials and anti-thrombotic blood diagnostic single-use plastic, metal or glass ware or use in regenerative medicine in the delivery of drugs or growth factors by surface grafted linear polysulfates.

Figure 17A:
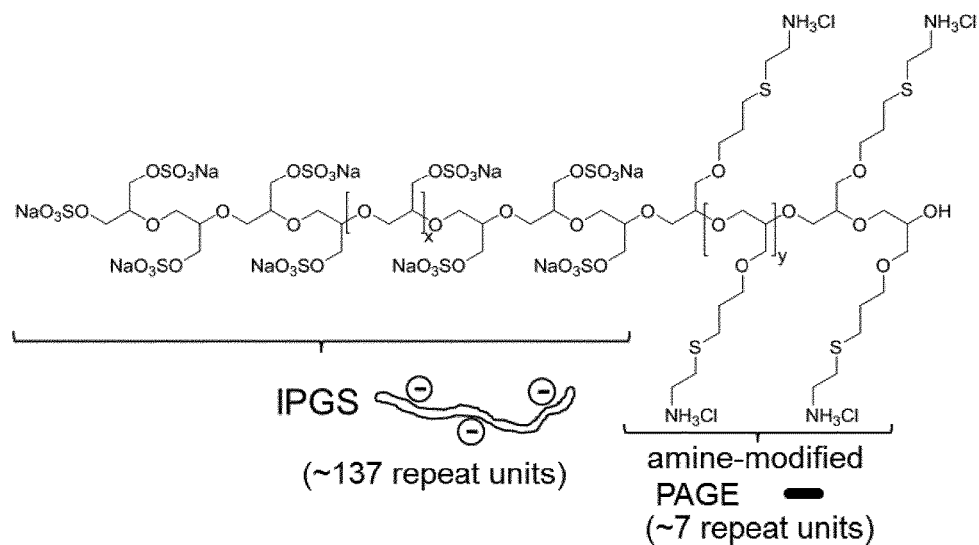
FIG. 17A shows a structure of an lPGS which is well suited for coating surfaces.

FIG. 17A shows the structure of an lPGS compound that is well suited for such coating applications. This lPGS compound is a terminally substituted lPGS, namely an lPGS-amine compound comprising poly allyl glycidyl ether (PAGE) blocks carrying amine groups.

Figure 17B:
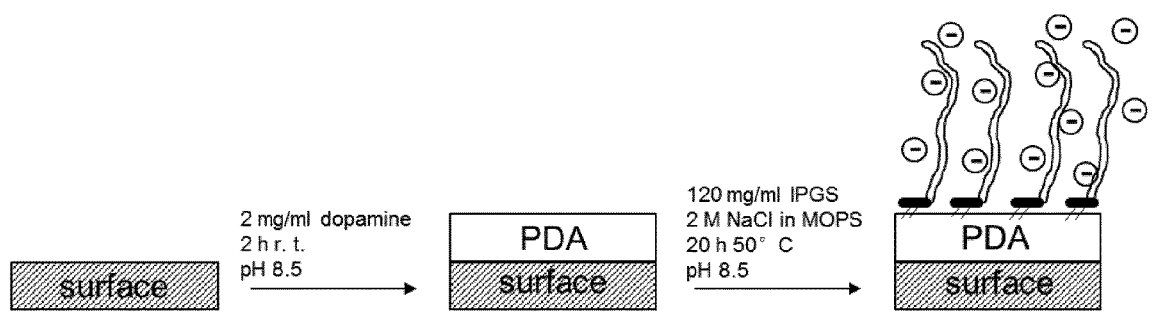
FIG. 17B shows a reaction scheme of a coating process.

These amine groups were used to covalently bond the lPGS to a layer of polydopamine (PDA) previously applied to a surface. An according reaction scheme is depicted in FIG. 17B. The surface coating by PDA was carried out according to a method described in literature (O. Pop-Georgievski et al, Langmuir 2012, 28, 14273-83). "MOPS" stands for 3-(N-morpholino)propanesulfonic acid, and "r.t." stands for room temperature.

Figure 18A:
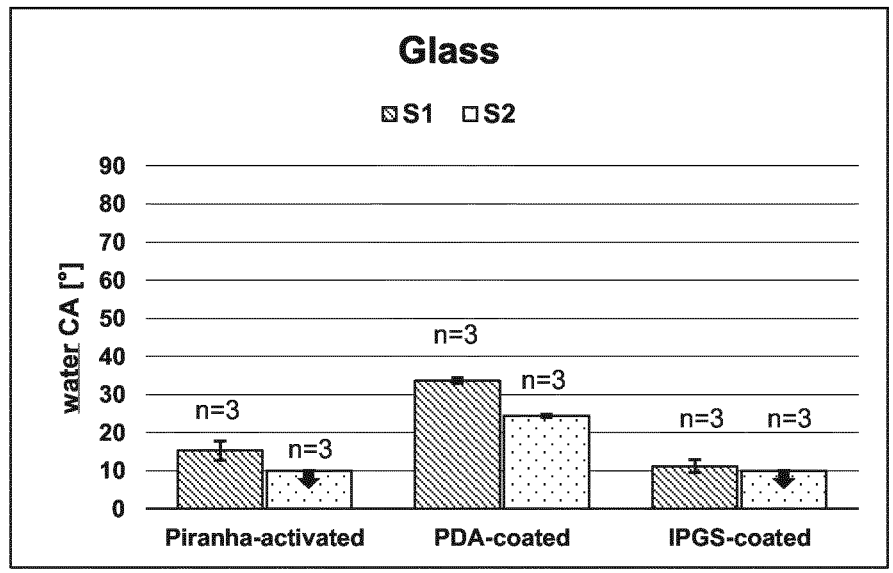
FIG. 18A shows the results of coating experiments in which a glass surface was coated by the lPGS of FIG. 17A.
Figure 18B:
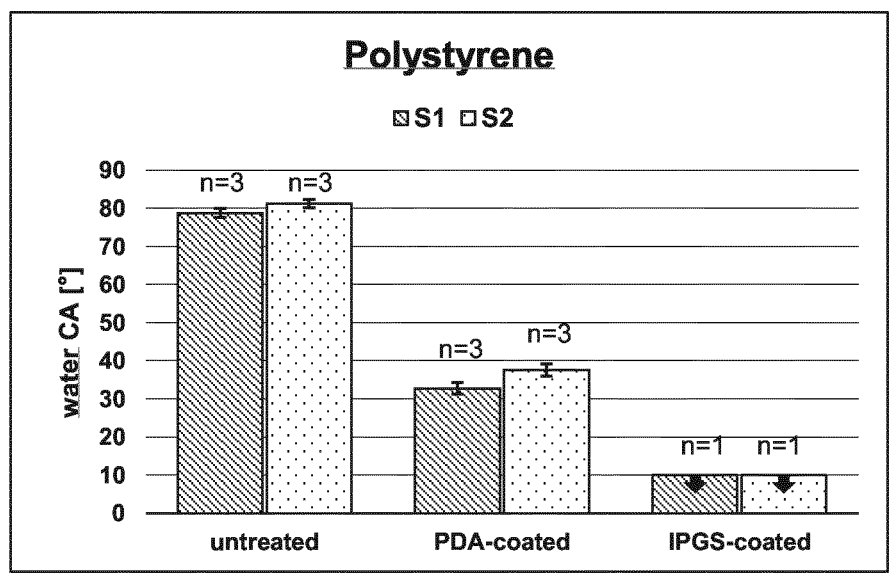
FIG. 18B shows the results of coating experiments in which a polystyrene surface was coated by the lPGS of FIG. 17A.
Figure 18C:
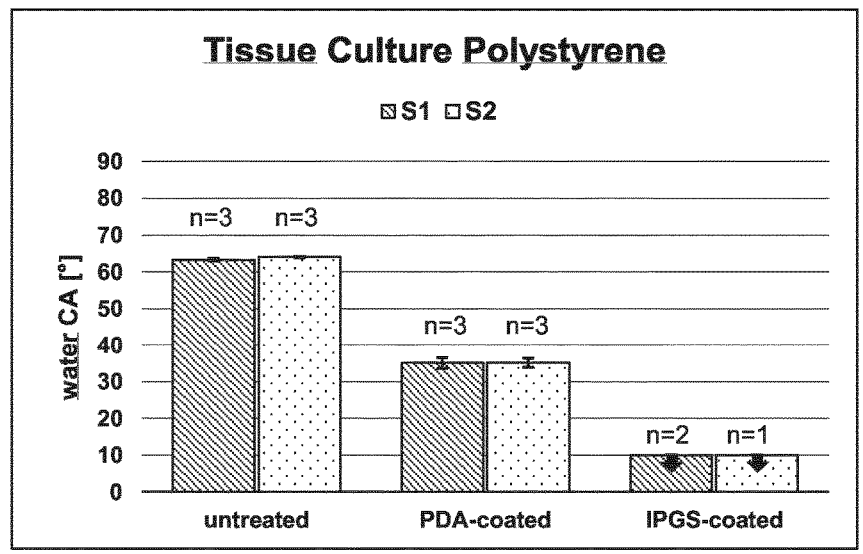
FIG. 18C shows the results of coating experiments in which a tissue culture polystyrene surface was coated by the lPGS of FIG. 17A.

Three different surfaces (namely, glass, polystyrene, and tissue culture polystyrene) were used for the coating experiments by the lPGS illustrated in FIGS. 17A and 17B. The results of these coating experiments are depicted in FIGS. 18A to 18C. A glass surface activated by piranha solution (piranha-activated glass surface) was used as control glass surface. Piranha solution is a mixture of sulfuric acid and hydrogen peroxide and is used to clean organic residues off substrates. The mixture is a strong oxidizing agent. It will remove most organic matter, and it will also hydroxylate most surfaces, making them highly hydrophilic.

The characterization of the surfaces was performed by measuring the water contact angle (CA) before the coating process, after coating with polydopamine (PDA) or after additional coating with lPGS. Thereby, two replicates were analyzed per surface (S1/S2) with n=3 CA per surface. Since a contact angle of below 10° cannot be measured precisely, contact angle values below 10° are indicated with a downward facing arrow in FIGS. 18A to 18C.

FIG. 18A shows the results of coating a glass surface. LPGS reduces the water contact angle in a similar way like piranha solution, but even stronger than piranha solution. The reduction of the contact angle with respect to a PDA coated surface is even stronger. Thus, lPGS is very well suited to hydrophilize a surface.

FIG. 18B shows the results of coating a polystyrene surface. While an untreated polystyrene surface has a water contact angle of approximately 80° (strongly hydrophobic), this water contact angle can be decreased by a PDA coating to values between 30° to 40°. In contrast, lPGS is able to reduce the water contact angle of values below 10°. Thus, lPGS is also well suited to hydrophilize a polystyrene surface.

The same holds true for a surface of tissue culture polystyrene. According results are depicted in FIG. 18C. Untreated tissue culture polystyrene surface has a water contact angle of approximately 65°. This water contact angle can be decreased by a PDA coating to approximately 35°. However, with an lPGS coating, the water contact angle is decreased to values below 10°. Thus, an lPGS coating makes a tissue culture polystyrene surface highly hydrophilic.

The stability of an according lPGS coating was tested on lPGS-coated glass surfaces by long-term incubation in different aqueous media.

In a first experiment, the lPGS-coated surface was incubated in $H_2O$ for 7 days and the water contact angle was measured afterwards.

In a second experiment, the same lPGS-coated surface was incubated in phosphate-buffered saline (PBS) for 7 days and the water contact angle was measured afterwards.

The results are depicted in the following table 11. Thereby, the number of measured droplets is given by n.

TABLE 11

| Water contact angles of lPGS-coated glass surface | | |
|---|---|---|
| Immediately after coating | After 7 days in $H_2O$ | After 7 days PBS |
| <10°(n = 3) | <10°(n = 3) | <10°(n = 3) |

These stability experiments show that the lPGS coating is very stable, even after prolonged incubation in an aqueous medium. Therewith, the lPGS coating is well suited to modify and therewith hydrophilize different surfaces.

Figure 19:
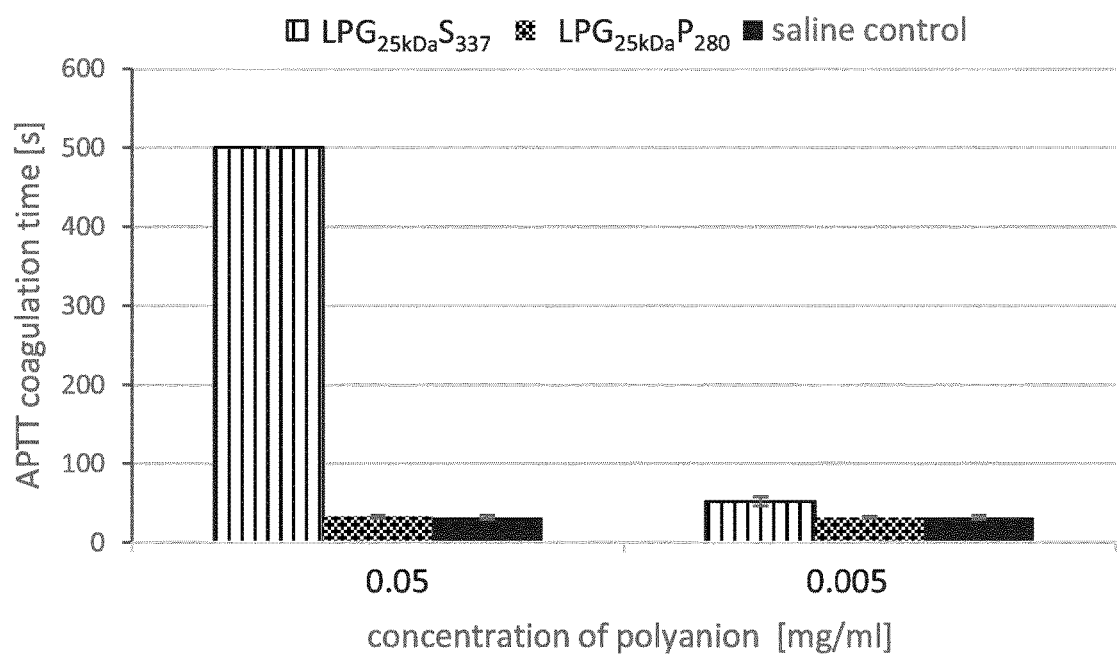
FIG. 19 shows a comparison between the anticoagulation effect of lPGS and of a linear polyglycerol phosphate.

FIG. 19 shows the anticoagulation effect of lPGS in comparison to a linear polyglycerol phosphate. Specifically, FIG. 19 depicts the aPTT coagulation time of human platelet poor plasma with linear polyglycerol sulfate $LPG_{25kDa}S_{337}$ and linear polyglycerol phosphate $LPG_{25kDa}P_{280}$ added at 0.05 and 0.005 mg/ml final concentration in plasma.

While the linear polyglycerol phosphate $LPG_{25kDa}P_{280}$ does not show any significant anticoagulative effect at the two concentrations, $LPG_{25kDa}S_{337}$ is able to strongly increase the coagulation time in the aPTT assay (for details of this assay, see above) already at a concentration of 0.005 mg/ml. At a concentration of 0.05 mg/ml the coagulation time is strongly increased by a factor of approximately 15 with respect to saline control or $LPG_{25kDa}P_{280}$, respectively. This data clearly shows the superiority of sulfate as substituent of the linear polyglycerol over other negatively charged groups such as phosphate.

Figure 20:
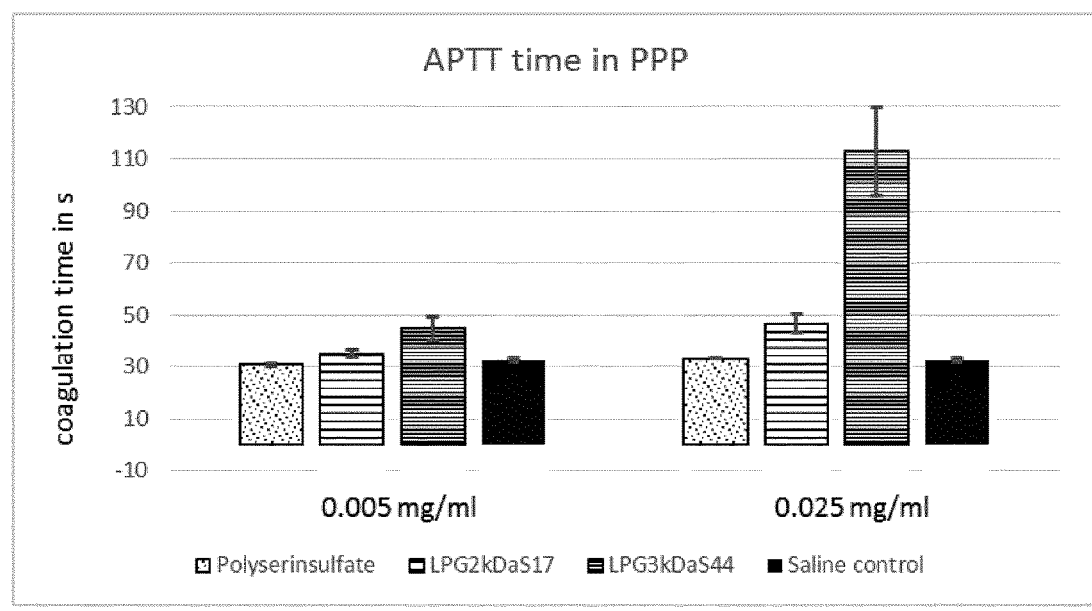
FIG. 20 shows aPPT plasma clotting times of different linear compounds.

The superiority of linear sulfated polyglycerols with respect to other linear sulfated compounds regarding coagulation inhibition can be seen in the results from an aPTT assay depicted in FIG. 20.

Sulfated polyserine (degree of sulfation dS=100%) has been subjected to an aPTT assay in PPP (details see above) in comparison to two different linear polyglycerol sulfates and to a saline control (negative control).

The non-sulfated precursor molecule polyserine has a molecular weight of approximately 2 kDa and can be described by the following formula:

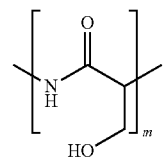

Upon sulfatation, the molecular weight increases to approximately 4 kDa.

FIG. 20 shows the aPTT coagulation times of PPP in the presence of sulfated polyserin, $LPG_{2kDa}S_{17}$ and $LPG_{3kDa}S_{44}$ at concentrations of 0.005 and 0.025 mg/ml with saline as negative control.

$LPG_{2kDa}S_{17}$ already shows in concentrations of 0.005 mg/ml an anti-coagulant effect with respect to the negative control. The anti-coagulant effect is even stronger for $LPG_{3kDa}S_{44}$. For both lPGS, the anti-coagulant effect increases with an increase in concentration to 0.025 mg/ml. In contrast, linear sulfated polyserine does not show an anti-coagulant effect. The coagulation time of PPP is not altered by sulfated polyserine, regardless if being used at a concentration of 0.005 mg/ml or 0.025 mg/ml.

The results of this experiment clearly show that a linear structure of a molecule and multivalently presented sulfate groups as such are not sufficient to obtain a compound having heparin-like properties. However, the claimed linear polyglycerol sulfates surprisingly have such heparin-like anti-coagulative properties and are well suited to be used as coagulation inhibitors.

But even in case of promising results of an aPTT assay indicating a good coagulation inhibition in PPP, an effective coagulation inhibition in whole blood can often not be foreseen by a person skilled in the art. In contrast to dendritic polyglycerol sulfates, linear polyglycerol sulfates do also show a favorable coagulation inhibition of whole blood, as shown in FIGS. 8 and 9. Therewith, the surprising properties of the claimed linear polyglycerol sulfates were not derivable by theoretic considerations but only by experiments such as those performed by the inventors.

PRIOR ART REFERENCES CITED IN THE PRESENT DOCUMENT

[1] J. Hirsh, S. S. Anand, J. L. Halperin, V. Fuster, *Circulation* 2001, 103, 2994-3018.

[2] R. De Caterina, S. Husted, L. Wallentin, G. Agnelli, F. Bachmann, C. Baigent, J. Jespersen, S. D. Kristensen, G. Montalescot, A. Siegbahn, F. W. A. Verheugt, J. Weitz, *Eur. Heart* 1 2007, 28, 880-913.

[3] J. W. Wilson, *J. Extra-Corp. Technol.* 1974, 6, 207-213.
[4] I.-K. Jang, M. J. Hursting, *Circulation* 2005, 111, 2671-2683.
[5] G. P. Visentin, M. Moghaddam, S. E. Beery, J. G. McFarland, R. H. Aster, *J. Lab. Clin. Med.* 2001, 138, 22-31.
[6] D. Hawkins, J. Evans, *Expert Opin. Drug Saf.* 2005, 4, 583-590.
[7] M. Pai, M. A. Crowther, *Handb. Exp. Pharmacol.* 2012, 207, 265-277.
[8] A. S. Fauci, E. Braunwald, D. L. Kasper, S. L. Hauser, D. L. Longo, L. J. Jameson, J. Loscalzo, *Harrison's Principles of Internal Medicine*, 17th Edition ed., Mc Graw Hill Medical, 2008.
[9] J. Hirsh, R. Raschke, *CHEST J.* 2004, 126, 188S-203S.
[10] M. Di Nisio, S. Middeldorp, H. R. Buller, *New Engl. J. Med.* 2005, 353, 1028-1040.
[11] S. M. Nimjee, C. P. Rusconi, R. A. Harrington, B. A. Sullenger, *Trends Cardiovas. Med.* 2005, 15, 41-45.
[12] D. Coombe, W. Kett, in *Heparin—A Century of Progress*, Vol. 207 (Eds.: R. Lever, B. Mulloy, C. P. Page), Springer Berlin Heidelberg, 2012, pp. 361-383.
[13] H. Türk, R. Haag, S. Alban, *Biocon. Chem.* 2004, 15, 162-167.
[14] M. Calderon, M. A. Quadir, S. K. Sharma, R. Haag, *Adv. Mater.* 2010, 22, 190-218.
[15] R. K. Kainthan, D. E. Brooks, *Biomaterials* 2007, 28, 4779-4787.
[16] R. K. Kainthan, S. R. Hester, E. Levin, D. V. Devine, D. E. Brooks, *Biomaterials* 2007, 28, 4581-4590.
[17] R. K. Kainthan, J. Janzen, E. Levin, D. V. Devine, D. E. Brooks, *Biomacromolecules* 2006, 7, 703-709.
[18] M. Weinhart, I. Grunwald, M. Wyszogrodzka, L. Gaetjen, A. Hartwig, R. Haag, *Chem.—Asian J.* 2010, 5, 1992-2000.
[19] R. Haag, M. Wyszogrodzka, M. Weinhart, *Production of linear, methylated polyglycerol derivatives for functionalization of surfaces in medical applications* 2007, DE 102006027125
[20] J. Dernedde, A. Rausch, M. Weinhart, S. Enders, R. Tauber, K. Licha, M. Schirner, U. Zuegel, A. von Bonin, R. Haag, *P. Natl. Acad. Sci. USA* 2010, 107, 19679-19684.
[21] R. Haag, J. Dernedde, R. Tauber, B. Gesche, S. Enders, H. Weinhart, *Dendritic polyglycerol sulfates and sulfonates and their use for inflammatory diseases* 2008, WO2007-EP6889.
[22] J. N. Kizhakkedathu, R. A. Shenoi, C. J. Carter, D. E. Brooks, *Polymers for reversing heparin-based anticoagulation* 2012, U.S. Pat. No. 8,637,008 B2.
[23] M. Gervais, A.-L. Brocas, G. Cendejas, A. Deffieux, S. Carlotti, *Macromol.* 2010, 43, 1778-1784.
[24] M. Gervais, A. Labbe, S. Carlotti, A. Deffieux, *Macromol.* 2009, 42, 2395-2400.
[25] A. Thomas, S. S. Müler, H. Frey, *Biomacromolecules* 2014, 15, 1935-1954.
[26] E. Gray, B. Mulloy, T. W. Barrowcliffe, *Thromb. Haemostasis* 2008, 99, 807-818.
[27] P. E. Bock, K. R. Srinivasan, J. D. Shore, *Biochemistry* 1981, 20, 7258-7266.
[28] R. A. Shenoi, M. T. Kalathottukaren, R. J. Travers, B. F. L. Lai, A. L. Creagh, D. Lange, K. Yu, M. Weinhart, B. H. Chew, C. Du, D. E. Brooks, C. J. Carter, J. H. Morrissey, C. A. Haynes, J. N. Kizhakkedathu *Sci. Transl. Med.* 2014 6, 260ra150.
[29] E. W. Davie, *J. Biol. Chem.* 2003, 278, 50819-50832.
[30] E. W. Davie, O. D. Ratnoff, *Science* 1964, 145, 1310-1312.
[31] K. A. Tanaka, N. S. Key, J. H. Levy, *Anesth. Analg.* 2009, 108, 1433-1446.
[32] T. Liu, C. D. Scallan, G. J. Broze, Jr., S. Patarroyo-White, G. F. Pierce, K. W. Johnson, *Thromb. Haemostasis* 2006, 95, 68-76.

The invention claimed is:

1. A linear polyglycerol compound, comprising an optionally terminally substituted backbone of linearly linked glycerol units, wherein it carries a plurality of sulfate substituents, wherein the degree of substitution of the backbone is between 10 and 100% %, wherein the linear polyglycerol compound has a structure according to one of the following formulae:

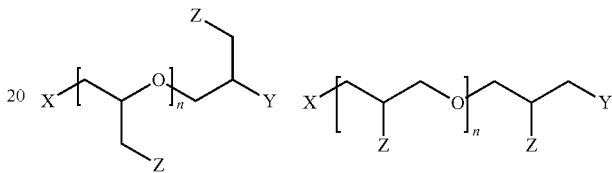

with
n=5 to 1000,
X, Y=independently from each other any organic residue with a functional group chosen from the group consisting of alcohol, amine, thiol, azide, alkyne, alkene, carboxylic acid, aldehyde, ketone, halogen, isocyanate, isothiocyanate, Michael acceptor/donor group,
Z=independently from other residues Z in the same polyglycerol molecule a negatively charged sulfate residue,
or an unreacted neutral precursor residue bearing a reactive of an alcohol, amine, thiol, halogen, azide, alkyne, alkene, carboxylic acid, or Michael acceptor/donor group,
wherein at least 10% of all residues Z in the polyglycerol are sulfate residues.

2. The linear polyglycerol compound according to claim 1, wherein the degree of substitution of the backbone is between 30 and 100%.

3. The linear polyglycerol compound according to claim 1, wherein the glycerol residues of the backbone are 1,2-linked or 1,3-linked to each other.

4. The linear polyglycerol compound according claim 1, wherein the backbone has a number average molecular weight of 1 kDa to 100 000 kDa.

5. The linear polyglycerol compound according to claim 1, wherein the backbone has a number average molecular weight of 2 kDa to 6 kDa and that the degree of substitution of the backbone is between 85 and 100%.

6. The linear polyglycerol compound according to claim 1, wherein the backbone has a number average molecular weight of 3 kDa to 5 kDa and that the degree of substitution of the backbone is between 85 and 100%.

7. The linear polyglycerol compound according to claim 1, wherein it is bound to a surface of an article.

8. A method for manufacturing a linear polyglycerol compound according to claim 1 comprising the following steps:
a) providing a linear polyglycerol compound, comprising a backbone of linearly linked glycerol residues bearing hydroxyl groups or other functional groups chosen from the group consisting of azides, alkynes, alkenes, thiols, halogens, primary or secondary amines, carboxylic acids, aldehydes, ketons and any Michael donor or acceptor for conjugation of anionically charged entities, and b) causing a reaction of at least some of these hydroxyl groups or these other functional groups of the linear polyglycerol compound provided in step a) with a compound introducing a negatively charged group into the linear polyglycerol compound, this compound being at least one chosen from the group consisting of sulfuric acid, sulfonic acid, a sulfuric acid derivative, and a sulfonic acid derivative.

9. A gel comprising a plurality of linear polyglycerol compounds according to claim 1, wherein it further comprises a crosslinker, wherein statistically each crosslinker molecule is covalently bound to one or more molecules of the linear polyglycerol compound.

10. A linear polyglycerol compound, comprising an optionally terminally substituted backbone of linearly linked glycerol units, wherein it carries a plurality of sulfate substituents, wherein the degree of substitution of the backbone is between 10 and 100%, wherein the linear polyglycerol compound has a structure according to one of the following formulae:

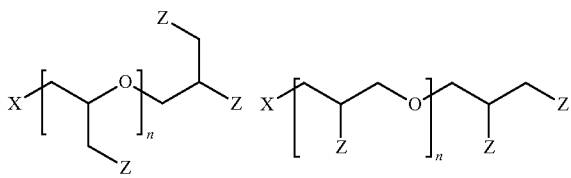

with
n=5 to 1000,
X=any organic residue with a functional group chosen from the group consisting of alcohol, amine, thiol, azide, alkyne, alkene, carboxylic acid, aldehyde, ketone, halogen, isocyanate, isothiocyanate, Michael acceptor/donor group, Z=independently from other residues Z in the same polyglycerol molecule a negatively charged sulfate residue,
or an unreacted neutral precursor residue bearing a reactive of an alcohol, amine, thiol, halogen, azide, alkyne, alkene, carboxylic acid, or Michael acceptor/donor group,
wherein at least 10% of all residues Z in the polyglycerol are sulfate residues.

11. The linear polyglycerol compound according to claim 10, wherein X denotes any organic residue with a functional group chosen from the group consisting of alcohol, amine, azide and halogen.

12. The linear polyglycerol compound according to claim 11, wherein the halogen is a bromine.

13. The linear polyglycerol compound according to claim 10, wherein X denotes any organic residue with a functional group chosen from the group consisting of alcohol and halogen.

14. The linear polyglycerol compound according to claim 10, wherein X denotes any organic residue with a functional group chosen from the group consisting of alcohol and azide.

15. The linear polyglycerol compound according to claim 10, wherein X denotes any organic residue with a functional group chosen from the group consisting of alcohol and amine.

16. The linear polyglycerol compound according to claim 10, wherein the linear polyglycerol compound has a structure according to the following formula:

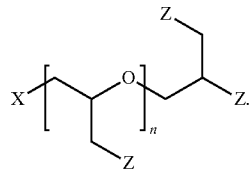

* * * * *